(12) United States Patent
Köster et al.

(10) Patent No.: US 7,038,103 B2
(45) Date of Patent: May 2, 2006

(54) SOLUTION PHASE BIOPOLYMER SYNTHESIS

(75) Inventors: Hubert Köster, La Jolla, CA (US); Ralf Wörl, Hamburg (DE)

(73) Assignee: Hubert Koster, Fingino (CH)

( * ) Notice: Subject to any disclaimer, the term of this patent is extended or adjusted under 35 U.S.C. 154(b) by 1117 days.

(21) Appl. No.: 09/484,484

(22) Filed: Jan. 18, 2000

(65) Prior Publication Data

US 2002/0007048 A1    Jan. 17, 2002

Related U.S. Application Data

(63) Continuation of application No. 09/067,337, filed on Apr. 27, 1998.

(51) Int. Cl.
*C07C 15/02* (2006.01)
*C07C 7/00* (2006.01)

(52) U.S. Cl. ............... 585/930; 585/932; 585/933; 585/934; 585/935; 585/400; 585/800

(58) Field of Classification Search ............ 536/4.1, 536/18.5, 18.4, 18.6, 25.3; 585/930, 932, 585/933, 934, 935, 400, 800
See application file for complete search history.

(56) References Cited

U.S. PATENT DOCUMENTS

| | | | |
|---|---|---|---|
| 4,749,742 A | 6/1988 | Elmore | 525/54.11 |
| 4,794,150 A | 12/1988 | Steel | 525/54.11 |
| 5,037,882 A | 8/1991 | Steel | 525/54.11 |
| 5,077,210 A | 12/1991 | Eigler et al. | 435/176 |
| 5,198,540 A * | 3/1993 | Koster | |
| 5,221,736 A | 6/1993 | Coolidge et al. | 536/25.31 |
| 5,246,840 A | 9/1993 | Nilsson | 435/101 |
| 5,262,331 A | 11/1993 | Salisbury et al. | 436/86 |
| 5,288,637 A | 2/1994 | Roth | 435/288 |
| 5,374,655 A | 12/1994 | Kashem et al. | 514/540 |
| 5,492,821 A | 2/1996 | Callstrom et al. | 435/188 |
| 5,532,147 A | 7/1996 | Nilsson | 435/100 |
| 5,539,083 A | 7/1996 | Cook et al. | 530/333 |
| 5,547,835 A | 8/1996 | Koster | 435/6 |
| 5,552,471 A | 9/1996 | Woo et al. | 524/494 |
| 5,552,535 A | 9/1996 | McLean et al. | 536/23.1 |
| 5,571,902 A | 11/1996 | Ravikumar et al. | 536/22.1 |
| 5,583,042 A | 12/1996 | Roth | 435/288.1 |
| 5,610,289 A | 3/1997 | Cook et al. | 536/25.34 |
| 5,616,698 A | 4/1997 | Krepinsky et al. | 536/18.6 |
| 5,616,700 A | 4/1997 | Reddy et al. | 536/25.3 |
| 5,635,488 A | 6/1997 | Cook et al. | 514/44 |
| 5,635,598 A | 6/1997 | Lebl et al. | 530/334 |
| 5,637,719 A | 6/1997 | Carpino et al. | 546/344 |
| 5,639,633 A | 6/1997 | Callstrom et al. | 435/68.1 |
| 5,641,862 A | 6/1997 | Rutter et al. | 530/334 |
| 5,644,029 A | 7/1997 | Carpino | 530/333 |
| 5,648,462 A | 7/1997 | Funakoshi et al. | 530/344 |
| 5,648,480 A | 7/1997 | Letsinger et al. | 536/25.34 |
| 5,652,358 A | 7/1997 | Pfleiderer et al. | 536/25.3 |
| 5,668,266 A | 9/1997 | Ruth | 536/25.3 |
| 5,679,773 A | 10/1997 | Holmes | 530/334 |
| 5,700,922 A | 12/1997 | Cook | 536/23.1 |
| 5,705,333 A | 1/1998 | Shah et al. | 435/6 |
| 5,705,621 A | 1/1998 | Ravikumar | 536/23.1 |
| 5,714,331 A | 2/1998 | Buchardt et al. | 435/6 |
| 5,719,262 A | 2/1998 | Buchardt et al. | 530/300 |
| 5,726,243 A | 3/1998 | Fields | 525/54.11 |
| 5,736,336 A | 4/1998 | Buchardt et al. | 435/6 |
| 5,736,625 A | 4/1998 | Callstrom et al. | 530/402 |
| 5,736,626 A | 4/1998 | Mullah et al. | 536/25.3 |
| 6,001,966 A * | 12/1999 | Pieken et al. | |

FOREIGN PATENT DOCUMENTS

| | | |
|---|---|---|
| EP | 0642798 | 3/1995 |
| WO | 8401779 | 5/1984 |
| WO | 8912624 | 12/1989 |
| WO | 9210092 | 6/1992 |
| WO | 9603148 | 2/1996 |
| WO | 9714706 | 4/1997 |
| WO | 9820166 | 5/1998 |
| WO | 9910362 | 3/1999 |
| WO | 9955718 | 12/1999 |

OTHER PUBLICATIONS

"IUPAC-IUB Commission on Biochemical Nomenclature Symbols for Amino-Acid Derivatives and Peptides Recommendations (1971)", *Biochem.*, 11(9):1726-1732 (1972).

Allin, S.M.and Shuttleworth, S.J., "The Preparation and First Application of a Polymer-Supported "Evans" Oxazolidinone", *Tetrahedron Lett.*, 37(44):8023-8026 (1996).

Backes, B.J. et al., "Activation Method to Prepare a Highly Reactive Acylsulfonamide "Safety Catch" Linker for Solid-Phase Synthesis[1]", *J. Am. Chem. Soc.*, 118:3055-3056 (1996).

(Continued)

*Primary Examiner*—James O. Wilson
*Assistant Examiner*—Paul V. Ward
(74) *Attorney, Agent, or Firm*—Stephanie Seidman; Fish & Richardson, P.C.

(57) ABSTRACT

Multifunctional liquid phase carriers (LPCs) and methods of using LPCs for the preparation of biopolymers are provided. The LPCs are highly symmetrical compounds that possess more than two points of attachment for biopolymer synthesis. The LPCs have the formula $Sp(X^1)_n$, where Sp is a highly symmetrical moiety such that all $X^1$ groups are equivalent. $X^1$ is a functional group that is suitable for biopolymer synthesis, including OH, SH, $NH_2$, COOH and the like. Biopolymers that may be produced using the methods provided include oligonucleotides, peptides, protein nucleic acids (PNAs) and oligosaccharides. Analogs of the biopolymers may also be prepared using the methods.

12 Claims, No Drawings

OTHER PUBLICATIONS

Batista-Viera, F. et al., "A New Method for Reversible Immobilization of Thiol Biomolecules Based on Solid-Phase Bound Thiolsulfonate Groups", *Appl. Biochem. Biotech.*, 31:175-195 (1991).

Beaucage, S.L. and Iyer, R.P., "The Synthesis of Modified Oligonucleotides by the Phosphoramidite Approach and Their Applications", *Tetrahedron*, 49(28):6123-6194 (1993).

Beaucage, S.L. and Caruthers, M.H., "Deoxynucleoside Phosphoramidites—A New Class of Key Intermediates for Deoxypolynucleotide Synthesis", *Tetrahedron Lett.*, 22(20): 1859-1862 (1981).

Beaucage, S.L. and Iyer, R.P., "The Functionalization of Oligonucleotides via Phosphoramidite Derivatives", *Tetrahedron*, 49(10):1925-1963 (1993).

Beaucage, S.L. and Iyer, R.P., "Advances on the Synthesis of Oligonucleotides by the Phosphoramidite Approach", *Tetrahedron*, 48(12):2223-2311 (1992).

Beck, S. and Koster, H., "Applications of Dioxetane Chemiluminescent Probes to Molecular Biology", *Anal. Chem.*, 62:2258-2270 (1990).

Bhargava, K.K. et al., "Synthesis of a Cyclic Analogue of Oxidized Glutathione by an Intersite Reaction in a Swollen Polymer Network", *J. Am. Chem. Soc.*, 105:3247-3251 (1983).

Biernat, J. et al., "Purification Orientated Synthesis of Oligodeoxynucleotides in Solution", *Tetrahedron Lett.*, 24(8):751-754 (1983).

Bray, A.M. et al., "Direct Cleavage of Peptides from a Solid Support into Aqueous Buffer. Application in Simulataneous Multiple Peptide Synthesis", *J. Org. Chem.*, 56:6659-6666 (1991).

Brown, E.L. et al., "Chemical Synthesis and Cloning of a Tyrosine tRNA Gene", *Meth. Enzymol.*, 68:109-151 (1979).

Brown, B.B. et al., "A single-bead decode strategy using electrospray ionization mass spectrometry and a new photolabile linker: 3-Amino-3-(2-nitrophenyl)propionic acid", *Mol. Divers.*, 1:4-12 (1995).

Brown, S.C. et al., "NMR Solution Structure of a Peptide Nucleic Acid Complexed with RNA", *Science*, 265:777-780 (1994).

Burgess, K. et al., "An Approach to Photolabile, Fluorescent Protecting Groups", *J. Org. Chem.*, 62:5165-5168 (1997).

Cardno, M. and Bradley, M., "A Simple Multiple Release System for Combinatorial Library and Peptide Analysis", *Tetrahedron Lett.*, 37(1):135-138 (1996).

Chan, W.C. and Mellor, S.L., "Reductive Alkylation of 9-Amino-xanthen-3-yloxymethylpoly(styrene): a Novel Procedure for the Synthesis of Peptidyl N-Alkyl Amides by Fmoc/Bu$^t$ Chemistry", *J. Chem. Soc. Chem. Commun.*, 1475-1476 (1995).

Cusack, N.J. et al., "Block Synthesis of Oligonucleotides by the Phosphotriester Approach", *Tetrahedron Lett.*, 24:2209-2212 (1973).

Database WPI, Derwent Publications #199612, citing International PCT application No. WO 96/03148 (item AT), published Jun. 25, 1992.

Database WPI, Derwent Publications #199848, citing Japanese Patent No. 10251292, published Sep. 22, 1998.

DeGrado, W.F. and Kaiser, E.T., "Polymer-Bound Oxime Esters as Supports for Solid-Phase Peptide Synthesis. Preparation of Protected Peptide Fragments", *J. Org. Chem.*, 45:1295-1300 (1980).

Eckstein, F., ed., "*Oligonucleotides and Analogues : A Practical Approach*", pp. 49-51; 58-59; 137-139; 255-259, IRL Press, Oxford, 1991.

English Language Abstract of Item EM: Wörl, R., "Entwicklung eines Konzeptes zur Oligonucleotidsynthese in Lösung nach der Phosphoamiditmethode", Ph.D. Dissertation, Hamburg, (1998).

English Language Abstract of Item CW: Köster, H. et al., "Synthesis of a Structural Gene for the Peptide Hormone Angiotensin II, Part I—Objective and Synthetic Strategy", *Liebigs Ann. Chem.*, 839-853, (1978).

Entwistle, I.D., "The Use of 2-Nitrophenylpropionic Acid as a protecting Group for Amino and Hydroxyl Functions to be Recovered by Hydrogen Transfer Reduction", *Tetrahedron Lett.*, 6:555-558 (1979).

Fattom, A. et al., "Comparative Immunogenicity of Conjugates Composed of the *Staphylococcus aureus* Type 8 Capsular Polysaccharide Bound to Carrier Proteins by Adipic Acid Dihydrazide or N-Succinimidyl-3-(2-Pyridyldithio)propionate", *Infection and Immun.*, 60(2):584-589 (1992).

Frechet, J.M.J. and Nuyens, L.J., "Use of Polymers as Protecting Groups in Organic Synthesis. III. Selective Functionalization of Polyhydroxy Alcohols", *Can. J. Chem.*, 54:926-934 (1976).

Froehler, B.C., "Deoxynucleoside H-Phosphonate Diester Intermediates in the Synthesis of Internucleotide Phosphate Analogues", *Tetrahedron Lett.*, 27(46):5575-5578 (1986).

Froehler, B.C. and Matteucci, M.D., "Nucleoside H-Phosphonates: Valuable Intermediates in the Synthesis of Deoxyoligonucleotides", *Tetrahedron Lett.*, 27(4):469-472 (1986).

Froehler, B.C. and Matteucci, M.D., "Substituted 5-Phenyltetrazoles: Improved Activators of Deoxynucleoside Phosphoramidites in Deoxyoligonucleotide Synthesis", *Tetrahedron Lett.*, 24(31):3171-3174 (1983).

Gait, M.J., ed., "*Oligonucleotide Synthesis : A Practical Approach*", IRL Practical Approach Series, IRL Press, Oxford, 1984.

Garegg, P.J. et al., "Nucleoside H-Phosphonates. III. Chemical Synthesis of Oligodeoxyribonucleotides by the Hydrogenphosphonate Approach", *Tetrahedron Lett.*, 27(34):4051-4054 (1986).

Gayo, L.M. and Suto, M.J., "Traceless Linker: Oxidative Activation and Displacement of a Sulfur-Based Linker", *Tetrahedron Lett.*, 38(2):211-214 (1997).

Goldmacher, V.S. et al., "Photoactivation of Toxin Conjugates", *Bioconj. Chem.*, 3:104-107 (1992).

Greene, T.W. "*Protective Groups in Organic Synthesis*", John Wiley and Sons, Inc., New York, 1981.

Han, Y. et al., "Silicon Directed *ipso*-Substitution of Polymer Bound Arylsilanes: Preparation of Biaryls via the Suzuki Cross-Coupling Reaction", *Tetrahedron Lett.*, 37(16):2703-2706 (1996).

Hazum, E. et al., "A Photocleavable Protecting Group for the Thiol Function of Cysteine", *Pept., Proc. Eur. Pept. Symp., 16th*, Brunfeldt, K. (ed.), pp 105-110, 1981.

Hermanson, G.T. "*Bioconjugate Techniques*", Academic Press, Inc., 1996.

Jones, R.A. et al., "use of the Lipophilic *tert*-Butyldiphenylsilyl Protecting Group in Synthesis and Rapid Separation of Polynucleotides", *Biochem.*, 17(7):1268-1277 (1978).

Jurnike, C. et al., "Detection of Hepatitis B Virus DNA in Serum Samples via Nested PCR and MALDI-TOF Spectrometry", *Genetic Anal: Biomol. Engg.*, 13:67-71 (1996).

Jurinke, C. et al., "Recovery of Nucleic Acids from Immobilized Biotin-Streptavidin Complexes using Ammonium Hydroxide and Applications in MALDI-TOF Mass Spectrometry", *Anal. Chem.*, 69:904-910 (1997).

Jurinke, C. et al., "Analysis of Ligase Chain Reaction Products via Matrix-Assisted Laser Desorption / Ionization Time-of-Flight- Mass Spectrometry", *Anal. Biochem.*, 237:174-181 (1996).

Kaldor, S.W. et al., "Use of Solid Supported Nucleophiles and Electrophiles for Purification of Non-Peptide Small Molecule Libraries", *Tetrahedron Lett.*, 37(40):7193-7196 (1996).

Khorana, H.G., "Total Synthesis of Gene", *Science*, 203:614-625 (1979).

Konig, B., et al., "alpha-Mannosyl clusters scaffolded on Azamacrocyles: Synthesis and inhibitory properties in the adhesion of type 1 fimbriated *Escherichia coli* to Guinea Pig erythrocytes", *Tetrahedron Letters*, 39(16):2307-2310 (1998).

Koster, H. et al., "Polymer Support Oligonucleotide Synthesis—XV: Synthesis of Oligodeoxynucleotides on Controlled Pore Glass (CPG) using Phosphate and a new Phosphotriester Approach", *Tetrahedron*, 40(1):103-112 (1984).

Koster, H. et al., "N-Acyl Protecting Groups for Deoxynucleosides: A Quantitative and Comparative Study", *Tetrahedron*, 37:363-369 (1981).

Koster, H. et al., "Some Improvements in the Synthesis of DNA of Biological Interest", *Nucl. Acids Res.*, Symposium Ser. 7:39-59 (1980).

Köster, H. et al., "Synthesis of a Structural Gene for the Peptide Hormone Angiotensin II, Part I—Objectives and Synthetic Strategy", *Liebigs Ann. Chem.*, 839-853, (1978).

Krchnak, V. et al., "Structurally Homogeneous and Heterogeneous Synthetic Combinatorial Libraries", *Mol. Divers.*, 1:149-164 (1995).

Kumar, G. and Poonian, M.S., "Improvements in Oligodeoxyribonucleotide Synthesis: Methyl N,N-Dialkylphosphoramidite Dimer Units for Solid Support Phosphite Methodology", *J. Org. Chem.*, 49:4905-4912 (1984).

Leznoff, C.C. and Wong, J.Y., "The Use of Polymer Supports in Organic Synthesis. The Synthesis of Monotrityl Ethers of Symmetrical Diols", *Can. J. Chem.*, 50:2892-2893 (1972).

Lloyd-Williams, P. et al., "Convergent Solid-Phase Peptide Synthesis", *Tetrahedron*, 49(48):11065-11133 (1993).

Lorsbach, B.A. et al., "Reissert-Based "Traceless" Solid-Phase Synthesis: Isoquinoline, and Isoxazoline-Containing Heterocycles", *J. Org. Chem.*, 61:8716-8717 (1996).

Maeji, N.J. et al., " Multi-pin Peptide Synthesis Strategy for T Cell Determinant Analysis", *J. immunol. Meth.*, 134:23-33 (1990).

Manoharan, M. et al., "A 2'-O-thiol Tether in the Ribose Moiety of Nucleic Acids for Conjugation Chemistry", *Gene*, 149:147-156 (1994).

McCray, J.A. and Trentham, D.R., "Properties and Uses of Photoreactive Caged Compounds", *Annu. Rev. Biophys. Biophys. Chem.*, 18:239-270 (1989).

Meltzer, A.D. et al., "Chain Dynamics in Poly(amido amine) Dendrimers. A Study of $^{13}$C NMR Relaxation Parameters", *Macromol.*, 25:4541-4548 (1992).

Milligan, J.F. et al., "Current Concepts in Antisense Drug Design", *J. Med. Chem.*, 36(14):1923-1937 (1993).

Morphy, J.R. et al., "A Novel Linker Strategy for Solid-Phase Synthesis", *Tetrahedron Lett.*, 37(18):3209-3212 (1996).

Mullis, K.B. and Faloona, F.A., "Specific Synthesis of DNA in Vitro via a Polymerase-Catalyzed Chain Reaction", *Meth. Enzymol.*, 155:335-350 (1987).

Mullis, K.B., "The Polymerase Chain Reaction (Nobel Lecture)", *Angew. Chem. Int. Ed. Engl.*, 33:1209-1213 (1994) (German Version: *Angew. Chem.*, 106:1271-1276 (1994)).

Newkome, G.R. et al., "Building Blocks for Dendritic Macromolecules", *Aldrichim. Acta*, 25(2):31-38 (1992).

Newkome, G.R. et al., "Polytryptophane Terminated Dendritic Macromolecules", *Tetrahedron: Asymm.*, 2(10):957-960 (1991).

Newkome, G.R. and Lin, X., "Symmetrical, Four-Directional, Poly(ether-amide) Cascade Polymers", *Macromol.*, 24:1443-1444 (1991).

Newlander, K.A. et al., "Simple Silyl Linker for the Solid Phase Organic Synthesis of Aryl-Containing Molecules", *J. Org. Chem.*, 62:6726-6732 (1997).

Nielsen, P.E. et al., "Sequence-Selective Recognition of DNA by Strand Displacement with a Thymine-Substituted Polyamide", *Science*, 254:1497-1500 (1991).

Norton, J.C. et al., "Targeting Peptide Nucleic Acid-Protein Conjugates to Structural Features within Duplex DNA", *Bioorg. Med. Chem.*, 3(4):437-445 (1995).

Olejnik, J. et al., "Photocleavable biotin phosphoramidite for 5'-end-labelling, affinity purification and phosphorylation of synthetic oligonucleotides", *Nucl. Acids Res.*, 24(2):361-366 (1996).

Patek, M. and Lebl, M., "Safety-Catch Anchoring Linkage for Synthesis of Peptide Amides by Boc / Fmoc Strategy", *Tetrahedron Lett.*, 32(31):3891-3894 (1991).

Peffer, N.J. et al., "Strand-invasion of Duplex DNA by Peptide Nucleic Acid Oligomers", *Proc. Natl. Acad. Sci. USA*, 90:10648-10652 (1993).

Plunkett, M.J. and Ellman, J.A., "A Silicon-Based Linker for Traceless Solid-Phase Synthesis", *J. Org. Chem.*, 60:6006-6007 (1995).

Pon, R.T., "Enhanced Copuling Efficiency using 4-Dimethylaminopyridine (DMAP) and either Tetrazole, 5-(o-Nitrophonyl)tetrazole, or 5-(p-Nitrophenyl)tetrazole in the Solid Phase Synthesis of Oligoribonucleotides by the phosphoramidite Procedure", *Tetrahedron Lett.*, 28(32):3643-3646 (1987).

Ritzen, A., et al., "Phenyltrisalanine: a new, C3-symmetric, trifunctional amino acid", *Tetrahedron: Asymmetry*, 9(19):3491-3496 (1998).

Routledge, A. et al,. "The Use of a Dithiane Protected Benzoin Photolabile Safety Catch Linker for Solid Phase Synthesis", *Tetrahedron Lett.*, 38(7):1227-1230 (1997).

Salmon, S.E. et al., "Discovery of Biologically Active Peptides in Random Libraries: Solution Phase Testing after Staged Orthogonal Release from Resin Beads", *Proc. Natl. Acad. Sci. USA*, 90:11708-11712 (1993).

Schmidt, J.G. et al., "Inforation Transfer from DNA to Peptide Nucleic Acids by Template-Directed Syntheses", *Nucl. Acids Res.*, 25(23):4792-4796 (1997).

Senter, P.D. et al., "Novel Photocleavable Protein Crosslinking Reagents and their use in the Preparation of Antibody-Toxin Conjugates", *Photochem. Photobiol.*, 42(3):231-237 (1985).

Shchepinov et al., "Oligonucleotide dendrimers: synthesis and use as polylabelled DNA probes", *Nucleic Acid Research*, 25(22):4447-4454 (1997).

Shinozuka, K., et al., "Novel multifunctional labelled DNA probe bearing an intercalator and a fluorophore", *Journal of The Chemical Society, Chemical Communications*, 11:1377-1378 (1994).

Siegert, C.W. et al., "Matrix-Assisted Laser Desorption / Ionization Time-of-Flight Mass Spectrometry for the Detection of Polymerase Chain Reaction Products Containing 7-Deazapurine Moieties", *Anal. Biochem.*, 243:55-65 (1996).

Sinha, N.D. et al., "Polymer Support Oligonucleotide Synthesis XVIII: Use of β-cyanoethyl-N,N-dialkylamino-/N-morpholino Phosphoramidite of Deoxynucleosides for the Synthesis of DNA Fragments Simplifying Deprotection and Isolation of the Final Product", *Nucl. Acids Res.*, 12(11):4539-4557 (1984).

Sinha, N.D. et al., "β-Cyanoethyl N,N-Dialkylamino/N-Morpholinomonochloro Phosphoamidites, New Phosphitylating Agents Facilitating Ease of Deprotection and Work-up of Synthesized Oligonucleotides", *Tetrahedron Lett.*, 24(52)5843-5846 (1983).

Sonveaux, E., "The Organic Chemistry Underlying DNA Synthesis", *Bioorg. Chem.*, 14:274-325 (1986).

Thiem, J. et al., "Novel Glycals as Synthons for Saccharide Syntheses", *Angew. Chem. Int. Ed. Engl.*, 18(3):222-223 (1979).

Tuchscherer, G., et al., "Templates in protein de novo design", *Journal of Biotechnology*, 41(2):197-210 (1995).

Uhlmann, E. and Peyman, A., "Antisense Oligonucleotides: A New Therapeutic Principle", *Chem. Rev.*, 90(4):543-584 (1990).

van Maarseveen, J.H. et al., "Solid Phase Ring-Closing Metathesis: Cyclization / Cleavage Approach towards a Seven Membered Cycloolefin", *Tetrahedron Lett.*, 37(45): 8249-8252 (1996).

Virnekas, B. et al., "Trinucleotide Phosphoramidities: Ideal Reagents for the Synthesis of Mixed Oligonucleotides for Random Mutagenesis", *Nucl. Acids Res.*, 22(25):5600-5607 (1994).

Wolter, A. et al., "Polymer Support Oligonucleotide Synthesis XX[1]: Synthesis of a Henhectacosa Deoxynucleotide by use of a Dimeric Phosphoramidite Synthon", Nucleosides Nucleotides, 5(1):65-77 (1986).

Wong, S.S. "*Chemistry of Protein Conjugation and Cross-Linking*", CRC Press, Inc., 1991.

Wörl, R., "Entwicklung eines Konzeptes zur Oligonucleotidsynthese in Lösung nach der Phosphoamiditmethode", Ph.D. Dissertation, Hamburg, (1998).

Wörl, R. and Köster, H., "Synthesis of New Liquid Phase Carriers for Use in Large Scale Oligonucleotide Synthesis in Solution", *Tetrahedron* 55:2941-2956, (1999).

Wörl, R. and Köster, H., "The Use of Liquid Phase Carriers for Large Scale Oligonucleotide Synthesis in Solution via Phosphoamidite Chemistry", *Tetrahedron* 55:2957-2972, (1999).

Worster, P.M. et al., "Asymmetric Synthesis of 2-Alkylcyclohexanones on Solid Phases", *Angew. Chem. Int. Ed. Engl.*, 18(3):221-222 (1979).

Yen, H-R. et al., "Optically Controlled Ligand Delivery, 1. Synthesis of Water-Soluble Copolymers containing Photocleavable Bonds", *Makromol. Chem.*, 190:69-82 (1989).

Zuckermann, R. et al., "Efficient Methods for Attachment of Thiol Specific Probes to the 3'-ends of Synthetic Oligodeoxyribonucleotides", *Nucl. Acids Res.*, 15(13):5305-5321 (1987).

Yamagiwa, Y, et al.; "Synthesis of Imidazole Containing Ligands and Studies on Metal Complexes", Bull. Chem. Soc. Jpn., 69: 3317-3323, (1996).

Bradshaw J. and Krakowiak, K., "Facile Synthesis of Benzene-bridged Azaoxemecrobicyclic Ligands", 35:519 (1998).

Cochrane et al., "Synthesis of Symmetrically Trisubstituted Benzene Derivatives", J. Chem. Soc. (C), 1968.

* cited by examiner

SOLUTION PHASE BIOPOLYMER SYNTHESIS

RELATED APPLICATIONS

This application is a continuation of U.S. application Ser. No. 09/067,337, entitled "SOLUTION PHASE BIOPOLYMER SYNTHESIS" filed Apr. 27, 1998 to Hubert Köster and Ralf Wörl. The subject matter of U.S. application Ser. No. 09/067,337 is incorporated by reference in its entirety.

FIELD OF INVENTION

Liquid phase carriers (LPCs) and methods of use of LPCs in biopolymer synthesis are provided. In particular, multifunctional LPCs and methods of use of multifunctional LPCs in oligonucleotide synthesis are provided.

BACKGROUND OF THE INVENTION

Recent developments in chemistry and biology are indicative of an increased demand for modified biopolymers, such as oligonucleotides, peptides and oligosaccharides. For most applications, oligonucleotides are needed only in small amounts (nano- to milligrams), for use in, e.g., polymerase chain reactions (see, e.g., K. B. Mullis *Angew. Chem.* 1994, 106, 1271–1276 and K. B. Mullis et al. *Methods Enzymol.* 1987, 155, 335–3508) and as diagnostic tools (see, e.g., S. Beck et al. *Anal. Chem.* 1990, 62, 2258–2270; C. Jurinke et al. *Anal. Biochem.* 1996, 237, 174–181; C. Jurinke et al. *Genetic Analysis: Biomolecular Engineering* 1996, 13, 67–71; C. Jurinke et al. *Anal. Biochem.* 1997, 69, 904–910 and C. W. Siegert et al. *Anal. Biochem.* 1996, 243, 55–65).

There, however, is an increase in uses of biopolymers as therapeutic agents. For example, antisense oligonucleotides (see, e.g., E. Uhlmann et al. *Chem. Rev.* 1990, 90, 543–584 and F. F. Milligan et al. *J. Med. Chem.* 1993, 36, 1923–1937) may be used as therapeutic agents. Current methods of biopolymer synthesis, such as solid phase synthesis of oligonucleotides and peptides, result in preparation of small amounts of a desired biopolymer (see, e.g., N. D. Sinha et al. *Tetrahedron Lett.* 1983, 24, 5843–5846; H. Köster et al. *Tetrahedron* 1984, 40, 103–112; and N. D. Sinha et al. *Nucleic Acids Res.* 1984, 12, 4539–4557).

Thus, there is a need for economical large-scale methods of synthesis of modified biopolymers, such as oligonucleotides, peptides and oligosaccharides, that provide the biopolymer with the requisite high purity for therapeutic use. Synthesis in solution offers advantages in large scale production, such as easy upscaling, direct reaction control and purification after each reaction cycle, affording products of high purity. One drawback of solution phase synthesis lies in lower yields, caused by loss of product during purification and incomplete reactions, because reagents cannot be used in large excesses. Known methods of solution phase synthesis of biopolymers also suffer from loss of yield as the length of the biopolymeric chain increased.

A further drawback of solution phase techniques is the lack of solubility of the substrate biopolymer in organic solvents when the number of monomeric units exceeds 3–5. Such lack of solubility also contributes to lower yields seen in solution phase synthesis of biopolymers. Therefore, there is a need for carriers that mediate the solubility of the growing biopolymeric chain.

Therefore, it is an object herein to provide carriers for solution phase synthesis of biopolymers. It is also an object herein to provide methods for biopolymer synthesis using the carriers.

SUMMARY OF THE INVENTION

Liquid phase carriers (LPCs), LPCs coupled to biopolymers and methods of synthesis of biopolymers using LPCs are provided. In particular, biopolymers that can be prepared using the LPCs and methods described herein include, but are not limited to, oligonucleotides, peptides, peptide nucleic acids (PNAs) and oligosaccharides. A desired biopolymer may be prepared by the methods provided herein, or modification thereof using techniques known to those of skill in the art.

The LPCs provided herein are multifunctional compounds that allow for the simultaneous construction of three or more biopolymers, which may be of differing structure, but more typically are identical in structure.

The LPCs have the formula $Sp(X^1)_n$. Sp refers to a group that serves as the scaffold upon which synthesis of a plurality of oligomers is effected. $X_1$ is the reactive group for effecting synthesis of a selected biopolymer, and "n" is preferably 3 or more. In particular, Sp is a polyvalent group, such as an atomic group, a cyclic group or an aromatic group (heterocycles, carbocycles, aryls, heteroaryls, such that the resulting structure is symmetrically disposed around the center of the cyclic group), that has more than two points of attachment, n is the number of points of attachment in Sp, and is preferably 3–6, and $X^1$ is a reactive group for performing synthesis of a biopolymer. Sp is preferably a symmetrical group such that all $X^1$ groups are equivalent. It will be appreciated by those of skill in the art that such symmetry allows for uniformity in the synthesis of n biopolymers, where n is preferably 3 or more, using the LPCs provided herein. The LPCs provided herein are intended for use for synthesis of three or more biopolymers.

In one embodiment, the LPCs have one of formulae (I):

(Ia)

(Ib)

(Ic)

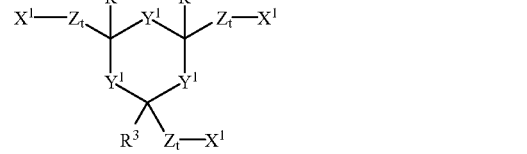
(Id)

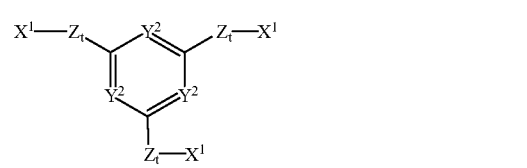
(Ie)

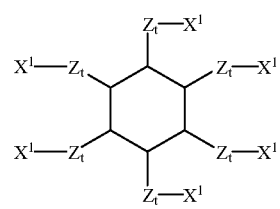

-continued

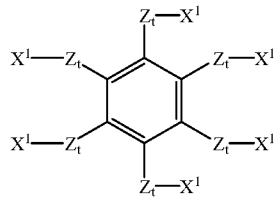
(If)

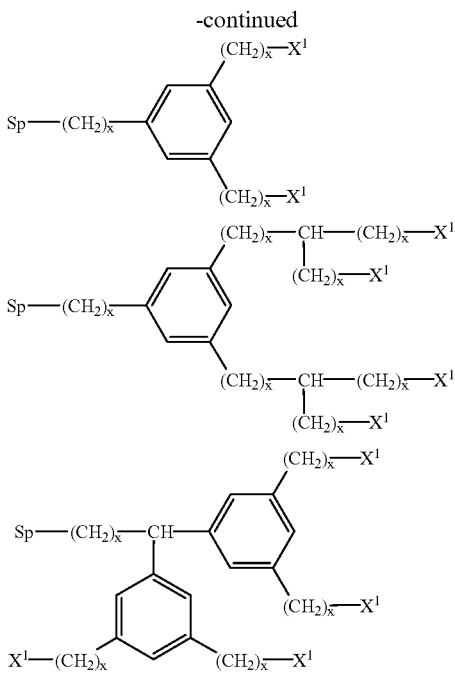

where Sp is $(R^1)_p$-A, E or a cyclic group (i.e. heterocycles, carbocycles, aryls, heteroaryls, such that the resulting structure is symmetrically disposed around the center of the cyclic group) with the linked "$Z_t$" moieties, where t is 0 or 1. As depicted the cyclic and aromatic rings have 6 members; it is understood that fewer or higher-number membered rings may also be used, as long as the resulting structure possesses the requisite symmetry, and the number of linkages for synthesis of the biopolymers is greater than two.

In particular, A is carbon or silicon; E is nitrogen or P(O); $R^1$ and $R^3$ are each independently hydrogen, alkyl, aryl, aralkyl, heteroaryl, heteroaralkyl, heterocyclyl or heterocyclylalkyl; p is 0 or 1; Z, where t is 0 or 1, is a divalent hydrocarbon, containing one or more or mixtures of phenylene or alkylene groups, and contains a sufficient number of carbons (0, where t is 0, up to as many as 24 or more) to prevent or to reduce interactions among the chains in each biopolymer during synthesis. Preferably Z, typically containing from 1 up to 30 carbons or more, is any combination alkylene and arylene units, preferably methylene and phenylene units, preferably 1–12, more preferably 2–12, particularly 3–12, more particularly 4–12, most preferably 6–12, 7–12 or 8–12 units, preferably selected from 1,2-, 1,3- or 1,4-, preferably 1,4-, phenylene and alkylene units, more preferably methylene units, which units may be combined in any order; $X^1$ is any reactive group that is used in biopolymer synthesis (see, e.g., U.S. Pat. No. 5,198,540, the disclosure of which is incorporated herein by reference), and is preferably halide, OH, SH, $NH_2$, $COR^5$ or $COOR^4$; n is preferably 3 or 4; $R^4$ is selected from hydrogen, alkyl, aryl, aralkyl, heteroaryl, heteroaralkyl, heterocyclyl and heterocyclylalkyl; $R^5$ is halide, heteroaryl or pseudohalide; $Y^1$ is $CH_2$, NH, S or O; and $Y^2$ is selected from CH and N.

In other embodiments, Z is a multivalent group, particularly a trivalent or higher valency hydrocarbon, with three or more points of attachment: The points of attachment are to A, E, or the cyclic nucleus, and the others are to two or more $X^1$ groups. In these embodiments, Z is chosen such that the symmetry of the LPC is maintained and all of the $X^1$ groups are equivalent.

Thus, the resulting LPCs, in these embodiments, are chosen from compounds such as, but not limited to, the following:

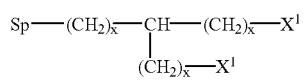

where Sp (i.e., $(R^1)_p$-A, E or the cyclic group with the linked "$Z_t$" moieties, where t is 0 or 1) and $X^1$ are chosen as above and x is preferably 0–12, more preferably 0–6.

In certain embodiments, the LPCs contain two or more of the compounds of formula (I) that are linked together so that the symmetry of the resulting LPC is maintained (i.e., all $X^1$ groups are equivalent). In preferred embodiments, the LPCs have formulae:

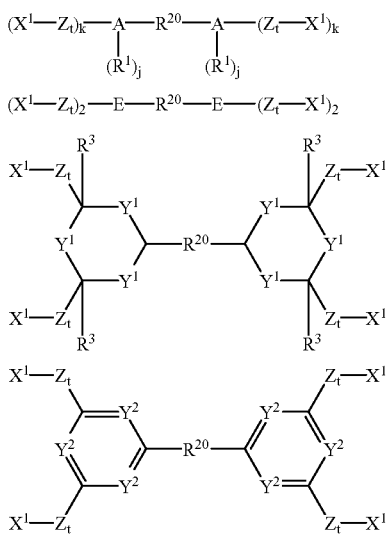

where A, E, $R^1$, $R^3$, $X^1$, $Y^1$, $Y^2$, t and Z are defined as for formula (I); $R^{20}$ is alkylene, alkenylene, alkynylene, arylene or heteroarylene of any desired length, preferably from 0 to 24, more preferably from 1 to about 12; k is 2 or 3; and j is 0 or 1.

Any of the groups $R^1$, $R^3$, $R^4$, $R^5$, $X^1$, $Y^1$, $Y^2$ and Z may be unsubstituted or substituted with one or more substituents each independently selected from Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl.

In certain embodiments, the LPCs are chosen as above, with the proviso that Z contains more than two methylene groups. In other embodiments, the LPCs are chosen with the proviso that Z is not 1,4-arylene. In more preferred embodiments, the LPCs are chosen with the proviso that Z contains more than two methylene groups and is not 1,4-arylene. In other more preferred embodiments, the LPCs are chosen with the proviso that Z contains at least one, preferably at least two, more preferably at least three or more phenylene or alkylene units.

Methods of synthesis of biopolymers using the LPCs described herein are also provided. The LPCs and methods permit synthesis of relatively large amounts, i.e. therapeutically useful amounts or preparative amounts (on the order of at least 0.1 grams, preferably a gram or more in volumes at which solid phase methods and other liquid phase methods produce substantially lower amounts) of biopolymers, including, but not limited to, oligonucleotides, peptides, peptide nucleic acids (PNAs) and oligosaccharides, may be produced by the methods. It is possible to prepare not only naturally occurring biopolymers, but also analogs of the biopolymers. Such analogs include, for example, analogs of oligonucleotides such as oligo-triesters or oligophosphonates. Use of the LPCs provided herein in the methods afford biopolymers of high purity and in significantly higher yields than methods known in the art.

In one embodiment, the methods involve the steps of (a) reacting an LPC of formula $Sp(X^1)_n$, provided herein, with a first monomer $N^1$; (b) separating and purifying the product of step (a) to afford a compound of formula $Sp(X^1-N^1)_n$; (c) reacting the product of step (b) with a second monomer $N^2$, a dimer $N^2-N^3$ or a trimer $N^2-N^3-N^4$; and (d) repeating steps (b) and (c) using the desired monomers, dimers or trimers to produce the desired LPC-bound biopolymer of formula $Sp(X^1-N^1-N^2-\ldots-N^m)_n$, where m is 3 to 100, preferably 3–50, more preferably 3–25, most preferably 3–10. In another embodiment, the methods further involve the step of (e) cleaving the biopolymer from the LPC.

In another embodiment, the methods involve the steps of:

(a) reacting an LPC of formula $Sp(X^1)_n$ with a first monomer $N^1$;

(b) separating and purifying the product of step (a) to afford a compound of formula $Sp(X^1-N^1)_n$;

(c) reacting the product of step (b) with a second monomer $N^2$, a dimer $N^2-N^3$ or a trimer $N^2-N^3-N^4$; and (d) repeating steps (b) and (c) to produce an LPC-bound biopolymer, preferably an oligonucleotide, of formula $Sp(X^1-N^1-N^2-\ldots-N^m)_n$, where m is 3 to 100, wherein:

Sp is a polyvalent group that has two or more points of attachment, n corresponds to the number of points of attachment in Sp and $X^1$ is a reactive group for biopolymer, preferably oligonucleotide, synthesis;

$N^1, N^2, N^3 \ldots N^m$ are biopolymer monomers, preferably nucleotides or nucleosides;

the dimers and trimers comprise the monomers; and the protocol used in steps (c) and (d) to synthesize the biopolymer, preferably the oligonucleotide, is the phosphoramidite protocol.

Monomers (N) used in preparing the biopolymer will depend on the biopolymer desired. For example, monomers which are used in the methods include nucleotides, nucleosides, natural and unnatural amino acids, PNA monomers and monosaccharides. In the methods, synthesis of the biopolymeric chain (i.e, steps c and d) may be performed by any protocol known to those of skill in the art. A preferred protocol for oligonucleotide synthesis is the phosphoramidite protocol (see, e.g., S. L. Beaucage et al. *Tetrahedron* 1992, 48, 2223–2311 and S. L. Beaucage et al. *Tetrahedron Lett.* 1981, 22, 1859–1862).

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, peptide nucleic acid (PNA) refers to nucleic acid analogs in which the ribose-phosphate backbone is replaced by a backbone held together by amide bonds.

As used herein, MALDI-TOF refers to matrix assisted laser desorption ionization-time of flight mass spectrometry.

As used herein, a liquid phase carrier (LPC) is a symmetrical compound that possesses functionality compatible with biopolymer synthesis. Such functionality includes, but is not limited to, alcohol, thiol, amino, carboxylic acid, acyl halide, ester, acyl heteroaryl and acyl pseudohalide groups. Preferably, the symmetry of the LPC is such that all of the functional groups are equivalent. Multifunctional LPCs are LPCs that possess three or more functional groups for use in biopolymer synthesis.

As used herein, a biopolymer is any compound found in nature, or derivatives thereof, made up of monomeric units. Biopolymers include, but are not limited to, oligonucleotides, peptides, peptide nucleic acids (PNAs) and oligosaccharides. Thus, the monomeric units include, but are not limited to, nucleotides, nucleosides, amino acids, PNA monomers, monosaccharides, and derivatives thereof.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 1 to 16 carbons preferably contain 1 to 5 double bonds. Alkynyl carbon chains of from 2 to 20 carbons preferably contain 1 to 8 triple bonds, and the alkynyl carbon chains of 2 to 16 carbons preferably contain 1 to 5 triple bonds. The alkyl, alkenyl and alkynyl groups may be optionally substituted, with one or more groups, preferably alkyl group substituents that may be the same or different. As used herein, lower alkyl, lower alkenyl, and lower alkynyl refer to carbon chains having less than about 6 carbons.

As used herein, an "alkyl group substituent" includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 3 to 19 carbon atoms. Aryl groups include, but are not limited to groups, such as phenyl, substituted phenyl, naphthyl, substituted naphthyl, in which the substituent is lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, arylalkyl, heteroarylalkyl, alkenyl containing 1 to 2 double bonds, alkynyl containing 1 to 2 triple bonds, halo, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "cycloalkyl" refers to a saturated mono- or multicyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged or spiro-connected fashion, and may be optionally substituted with one or more alkyl group substituents.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl may be optionally substituted with one or more, preferably 1 to 3, aryl group substituents. Exemplary heteroaryl groups include, for example, furyl, imidazinyl, pyrrolidinyl, pyrimidinyl, tetrazolyl, thienyl, pyridyl, pyrrolyl, N-methylpyrrolyl, quinolinyl and isoquinolinyl, with pyridyl and quinolinyl being preferred.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle may be optionally substituted with one or more, preferably 1 to 3 aryl group substituents. Preferred substituents of the heterocyclic group include hydroxy, amino, alkoxy containing 1 to 4 carbon atoms, halo lower alkyl, including trihalomethyl, such as trifluoromethyl, and halogen. As used herein, the term heterocycle may include reference to heteroaryl.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" refers to —S(O)—. As used herein, "sulfonyl" refers to —S(O)$_2$—.

As used herein, "aminocarbonyl" refers to —C(O)NH$_2$.

As used herein, "alkylaminocarbonyl" refers to —C(O)NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O)NRR' in which R and R' are independently selected from aryl, preferably lower aryl, more preferably phenyl.

As used herein, "arylalkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulphur or substituted or unsubstituted nitrogen atoms, where the nitrogen substituent is alkyl as previously described. Exemplary alkylene groups include methylene (—$CH_2$—), ethylene (—$CH_2CH_2$—), propylene (—$(CH_2)_3$—), cyclohexylene (—$C_6H_{10}$—), methylenedioxy (—O—$CH_2$—O—) and ethylenedioxy (—O—$(CH_2)_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 2 to about 20 carbon atoms and at least one double bond, more preferably 1 to 12 carbons, even more preferably lower alkenylene. The alkenylene group is optionally substituted with one or more "alkyl group substituents." There may be optionally inserted along the alkenylene group one or more oxygen, sulphur or substituted or unsubstituted nitrogen atoms, where the nitrogen substituent is alkyl as previously described. Exemplary alkenylene groups include —CH═CH—CH═CH— and —CH═CH—$CH_2$—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, bivalent aliphatic hydrocarbon group, preferably having from 2 to about 20 carbon atoms and at least one triple bond, more preferably 1 to 12 carbons, even more preferably lower alkynylene. The alkynylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—$CH_2$—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "arylene" refers to a monocyclic or polycyclic, preferably monocyclic, bivalent aromatic group, preferably having from 3 to about 20 carbon atoms and at least one aromatic ring, more preferably 3 to 12 carbons, even more preferably lower arylene. The arylene group is optionally substituted with one or more "alkyl group substituents." There may be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents.

As used herein, "alkylidene" refers to a bivalent group, such as ═CR'R", which is attached to one atom of another group, forming a double bond. Exemplary alkylidene groups are methylidene (═$CH_2$) and ethylidene (═$CHCH_3$). As used herein, "arylalkylidene" refers to an alkylidene group in which either R' or R" is and aryl group.

As used herein, "amido" refers to a bivalent group, either —C(O)NH— or —HNC(O)—. "Thioamido" refers to a bivalent group, either —C(S)CH— or — HNC(S)—. "Oxyamido" refers to a bivalent group, either —OC(O)NH— or —HNC(O)O—. "Thiaamido" refers to a bivalent group, either —SC(O)NH— or —HNC(O)S—. "Dithiaamido" refers to a bivalent group, either —SC(S)NH— or —HNC(S)S—. "Ureido" refers to the bivalent group —HNCONH—. "Thioureido" refers to the bivalent group —HNCSNH—.

As used herein, the term "amino acid" refers to α-amino acids which are racemic, or of either the D- or L-configuration.

As used herein, when any particular group, such as phenyl or pyridyl, is specified, this means that the group is unsubstituted or is substituted. Preferred substituents where not specified are halo, halo lower alkyl, and lower alkyl.

As used herein, preparative or therapeutically useful amounts are amounts sufficient for use of the resulting products as therapeutics in which mgs to gms are administered. Typically, such amounts are at least 0.1 gms per synthesis, more preferably about gms to kilograms. Use of the LPCs provided herein results in improved yields and thereby permits development of preparative scale syntheses.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11, 1726).

A. Multifunctional Liquid Phase Carriers

Liquid phase carriers for use in solution phase synthesis of biopolymers are provided. In particular, the LPCs provided herein are multifunctional LPCs that preferably possess three or more functional moieties for biopolymer synthesis. The biopolymers prepared on a given LPC may be of differing structure, but more typically are identical in structure.

The LPCs have the formula $Sp(X^1)_n$, wherein Sp is a polyvalent group that has more than two points of attachment, n corresponds to the number of points of attachment in Sp and $X^1$ is a reactive group that is compatible from the point of view of biopolymer chemistry. Sp is preferably a symmetrical group such that all $X^1$ groups are equivalent. It will be appreciated by those of skill in the art that such symmetry allows for uniformity in the synthesis of n biopolymers using these LPCs.

In preferred embodiments, multifunctional liquid phase carriers in which the groups $X^1$ can form a silyl ether, trityl ether or ester bond with the 3'- or 5'-hydroxyl groups of a nucleoside, nucleotide or oligonucleotide are used.

Examples of the reactive group $X^1$ which are customary in nucleotide chemistry are described in *Liebigs Ann. Chem.*

1978, 839–853 and in *Nucleic Acids Research, Symposium Series No.* 7, 1980, 39–59. Typical examples are, inter alia, the following:

1. Acid halides, in particular acid chlorides and acid bromides;
2. Carboxylic acid groups, which can react with 5'-OH groups, for example in the presence of condensing agents; they can also be converted into activated trityl chloride derivatives according to the following equation:

—COOH+Y—C$_6$H$_4$(C$_6$H$_5$)$_2$C—Cl-->—CO—Y'—C$_6$H$_4$(C$_6$H$_5$)$_2$C—Cl, wherein Y=OH, SH or NH$_2$; and Y'=O, S or NH;

3. Activated ester functions of the general formula —COOR'; and
4. OH, SH and NH$_2$ groups.

In another preferred embodiment, carrier molecules of the general formula Sp(OH)$_n$, and the corresponding thio and amino derivatives, are used directly in the provided methods if they are to react with reactive carboxyl groups. However, they are usually employed in the form of activated compounds, which can be obtained, for example, in the following manner:

a) by reaction with dicarboxylic acid anhydrides, for example succinic or adipic anhydride, according to the equation -Sp-OH+(OC—R—CO)$_2$O-->-Sp-O—CO—R—COOH; or b) by reaction with trityl derivatives according to the equation -Sp-OH+HOOC—C$_6$H$_4$(C$_6$H$_5$)$_2$COH-->-Sp-O—CO—C$_6$H$_4$(C$_6$H$_5$)$_2$C—OH-->Sp-O—CO—C$_6$H$_4$(C$_6$H$_5$)$_2$C—Cl;

this reaction can be carried out in the presence of a condensing agent or after conversion of the acid function into an acid chloride function; or c) by reaction with dichlorosiloxanes according to the general equation —OH+Z(Me)$_2$Si-A-Si(Me)$_2$Z-->—O—Si(Me)$_2$-A-Si(Me)$_2$Z, wherein A is alkylene, arylene, —O— or a combination of these groups and Z is halogen; or d) by reaction with hydroxyl-substituted trityl derivatives, to form trityl ether derivatives, for example of the general formula -Sp-O—C$_6$H$_4$(C$_6$H$_5$)$_2$C—OH (-->-Sp-O—C$_6$H$_4$(C$_6$H$_5$)$_2$C—Cl); or e) by reaction with, for example, acrylonitrile, followed by alcoholysis of the nitrile and reaction of the resulting ester with an α,ω-diamine, to form amino derivatives, for example of the general formula -Sp-O—(CH$_2$)$_2$—C(O)—NH—(CH$_2$)$_x$—NH$_2$ wherein x is 0–6. The amine is then further derivatized according to any of a) through d), above, prior to biopolymer synthesis.

If the corresponding thio or amino derivatives are used, the corresponding S or N compounds are formed.

In selecting the group Sp, it is particularly essential that the carrier molecule Sp(X$^1$)$_n$ and its derivatives obtained in the course of biopolymer synthesis are soluble in the particular reaction medium used and can be chromatographed.

In one embodiment, the LPCs have formulae (I):

(Ia)

(Ib)

(Ic)

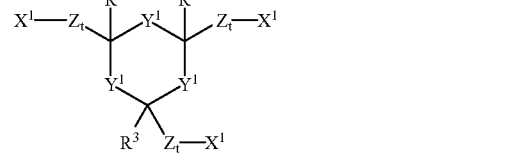

(Id)

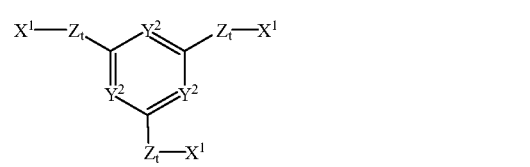

(Ie)

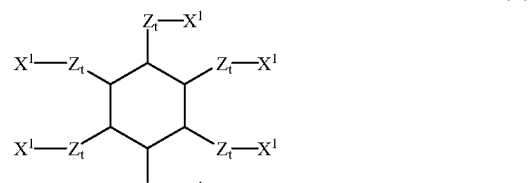

(If)

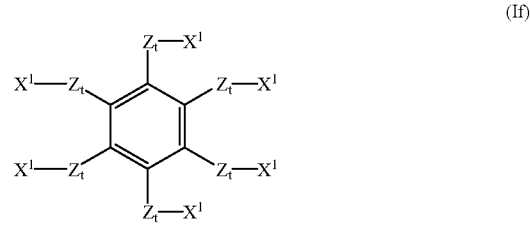

where A is carbon; E is nitrogen; R$^1$ and R$^3$ are each independently hydrogen, alkyl, aryl, aralkyl, heteroaryl, heteroaralkyl, heterocyclyl or heterocyclylalkyl; p is 0 or 1; Z is a divalent hydrocarbon as described above, and is preferably any combination of 0–12, preferably 1–12, more preferably 2–12, particularly 3–12, more particularly 4–12, most preferably 6–12, 7–12 or 8–12 units in which each unit is preferably selected from 1,4-phenylene and methylene, which units may be combined in any order; t is 0 or 1; X$^1$ is any reactive group which can be used in biopolymer synthesis (see, e.g., U.S. Pat. No. 5,198,540, the disclosure of which is incorporated herein by reference), and is preferably halide, OH, SH, NH$_2$, COR$^5$ or COOR$^4$; n is 3 or 4; R$^4$ is selected from hydrogen, alkyl, aryl, aralkyl, heteroaryl, heteroaralkyl, heterocyclyl and heterocyclylalkyl; R$^5$ is halide, heteroaryl or pseudohalide; Y$^1$ is CH$_2$, NH, S or O; and Y$^2$ is selected from CH and N.

Any of the groups R$^1$, R$^3$, R$^4$, R$^5$, X$^1$, Y$^1$, Y$^2$ and Z may be unsubstituted or substituted with one or more substituents each independently selected from Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl.

In embodiments where $X^1$ is halide, preferably chloride, Q is preferably selected from groups that are electron donating. Such groups include alkyl, alkoxy, dialkylamino, diarylamino, alkylarylamino, alkylthio and arylthio, with alkoxy, preferably methoxy, being preferred.

In certain embodiments, the LPCs are chosen as above, with the proviso that Z contains more than two methylene groups. In other embodiments, the LPCs are chosen with the proviso that Z is not 1,4-arylene. In other preferred embodiments, the LPCs are chosen with the proviso that Z contains more than two methylene groups and is not 1,4-arylene. In other more preferred embodiments, the LPCs are chosen with the proviso that Z contains at least one, preferably at least two, more preferably at least three or more phenylene or alkylene units.

1. Acyclic Multifunctional LPCs

In one embodiment, the LPCs are acyclic, multifunctional compounds in which all of the functional groups are equivalent. These LPCs generally have a center of symmetry at a single atom. In particular, the LPCs have formulae (IIa) or (IIb):

$(R^1)_p$—C-$(Z_t$-$X^1)_n$    (IIa)

N-$(Z_t$-$X^1)_3$    (IIb)

where $R^1$ is hydrogen, alkyl, aryl, aralkyl, heteroaryl, heteroaralkyl, heterocyclyl or heterocyclylalkyl; p and t are each independently 0 or 1; Z is any combination of phenylene and methylene units, selected from 0–12, preferably 1–12, more preferably 2–12, particularly 3–12, more particularly 4–12, most preferably 6–12, 7–12 or 8–12, units selected from 1,4-phenylene and methylene, which units may be combined in any order; $X^1$ is any reactive group that is used in biopolymer synthesis (see, e.g., U.S. Pat. No. 5,198,540, the disclosure of which is incorporated herein by reference), and is preferably OH, SH, $NH_2$, $COR^5$ or $COOR^4$; n is 3 or 4; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In preferred embodiments, the LPCs are of formula (IIa) wherein p is 0 or 1, preferably 0, and n is 3 or 4, preferably 4. Thus in more preferred embodiments, the LPCs of formula (IIa) have the formula C-$(Z-X^1)_4$, where Z is any combination of 0–12, preferably 1–12, more preferably 2–12, particularly 3–12, more particularly 4–12, most preferably 6–12, 7–12 or 8–12, units selected from 1,4-phenylene and methylene, which units may be combined in any order; $X^1$ is any reactive group which can be used in biopolymer synthesis (see, e.g., U.S. Pat. No. 5,198,540, the disclosure of which is incorporated herein by reference), and is preferably OH, SH, $NH_2$, $COR^5$ or $COOR^4$; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In more preferred embodiments, the LPCs of formula (IIa) have the formula C-$(Z-X^1)_4$, where Z is $C_{1-12}$, preferably $C_{2-12}$, more preferably $C_{3-12}$, particularly $C_{4-12}$, most preferably $C_{6-12}$, $C_{7-12}$ or $C_{8-12}$ alkylene and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide.

In particularly preferred embodiments, the LPCs of formula (IIa) have the formula C-$(Z-X^1)_4$, where Z is $C_{3-12}$, particularly $C_{4-12}$, most preferably $C_{6-12}$, $C_{7-12}$ or $C_{8-12}$ alkylene and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is OH, SH or $NH_2$, preferably OH.

In other particularly preferred embodiments, the LPCs of formula (IIa) have the formula C-$(Z-X^1)_4$, where Z is methylene or ethylene, preferably methylene, and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is OH, SH or $NH_2$, preferably OH. The presently most preferred LPC of formula (IIa) is pentaerythritol.

In other preferred embodiments, the LPCs are of formula (IIb) where Z is any combination of 0–12, preferably 1–12, more preferably 2–12, particularly 3–12, more particularly 4–12, most preferably 6–12, 7–12 or 8–12, units selected from 1,4-phenylene and methylene, which units may be combined in any order; $X^1$ is any reactive group which can be used in biopolymer synthesis (see, e.g., U.S. Pat. No. 5,198,540, the disclosure of which is incorporated herein by reference), and is preferably OH, SH, $NH_2$, $COR^5$ or $COOR^4$; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In more preferred embodiments, the LPCs have formula (IIb), where Z is $C_{1-12}$, preferably $C_{2-12}$, more preferably $C_{3-12}$, particularly $C_{4-12}$, most preferably $C_{6-12}$, $C_{7-12}$ or $C_{8-12}$ alkylene and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide.

In particularly preferred embodiments, the LPCs have formula (IIb), where Z is $C_{3-12}$, particularly $C_{4-12}$, most preferably $C_{6-12}$, $C_{7-12}$ or $C_{8-12}$ alkylene and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is OH, SH or $NH_2$, preferably $NH_2$.

In other particularly preferred embodiments, the LPCs have formula (IIb), where Z is methylene or ethylene, preferably ethylene, and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is OH, SH or $NH_2$, preferably $NH_2$. The presently most preferred LPC of formula (IIb) is tri(2-aminoethyl)amine.

In certain embodiments, the LPCs of formulae (IIa) and (IIb) are chosen as above, with the proviso that Z contains more than two, preferably more than three, more preferably more than four methylene groups. In other embodiments, the LPCs are chosen with the proviso that Z is not 1,4-arylene. In other preferred embodiments, the LPCs are chosen with the proviso that Z contains more than two methylene groups and is not 1,4-arylene. In other more preferred embodiments, the LPCs are chosen with the proviso that Z contains at least one, preferably at least two, more preferably at least three or more phenylene or alkylene units.

2. Cyclic Multifunctional LPCs

In another embodiment, the LPCs are cyclic, multifunctional compounds in which all of the functional groups are equivalent. These LPCs generally have a center of symmetry at the center of a core cycloalkyl, heterocyclyl, aryl or heteroaryl ring.

a. Cyclic Multifunctional LPCs of Formulae (IIc) or (IId)

In more preferred embodiments, the LPCs have formulae (IIc) or (IId):

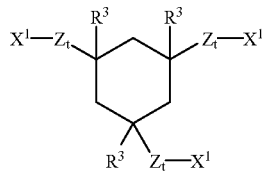
(IIc)

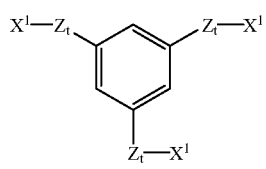
(IId)

where Z is any combination alkylene and phenylene units, of 0–12 units, preferably 1–12, more preferably 2–12, particularly 3–12, more particularly 4–12, most preferably 6–12, 7–12 or 8–12 units, preferably selected from 1,4-phenylene and methylene, which units may be combined in any order; t is 0 or 1; $X^1$ is any reactive group which can be used in biopolymer synthesis (see, e.g., U.S. Pat. No. 5,198,540, the disclosure of which is incorporated herein by reference), and is preferably halide, OH, SH, $NH_2$, $COR^5$ or $COOR^4$; n is 3 or 4; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In other preferred embodiments, the LPCs are of formula (IIc) where Z is any combination of 0–12, preferably 1–12, more preferably 2–12, particularly 3–12, more particularly 4–12, most preferably 6–12, 7–12 or 8–12, units selected from 1,4-phenylene and methylene, which units may be combined in any order; t is 0 or 1; $X^1$ is any reactive group which can be used in biopolymer synthesis (see, e.g., U.S. Pat. No. 5,198,540, the disclosure of which is incorporated herein by reference), and is preferably halide, OH, SH, $NH_2$, $COR^5$ or $COOR^4$; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In more preferred embodiments, the LPCs have formula (IIc), where Z is $C_{1-12}$, preferably $C_{2-12}$, more preferably $C_{3-12}$, particularly $C_{4-12}$, most preferably $C_{6-12}$, $C_{7-12}$ or $C_{8-12}$ alkylene; t is 1; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide.

In particularly preferred embodiments, the LPCs have formula (IIc), where Z is $C_{3-12}$, particularly $C_{4-12}$, most preferably $C_{6-12}$, $C_{7-12}$ or $C_{8-12}$ alkylene; t is 1; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is $COR^5$ or $COOR^4$, preferably $COOR^4$.

In other particularly preferred embodiments, the LPCs have formula (IIc), where Z contains 0, 1 or 2 methylene units, preferably 0; t is preferably 0; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is $COR^5$ or $COOR^4$, preferably $COOR^4$.

In other preferred embodiments, the LPCs are of formula (IId) where Z is any combination of 0–12, preferably 1–12, more preferably 2–12, particularly 3–12, more particularly 4–12, most preferably 6–12, 7–12 or 8–12, units selected from 1,4-phenylene and methylene, which units may be combined in any order; t is 0 or 1; $X^1$ is any reactive group which can be used in biopolymer synthesis (see, e.g., U.S. Pat. No. 5,198,540, the disclosure of which is incorporated herein by reference), and is preferably halide, OH, SH, $NH_2$, $COR^5$ or $COOR^4$; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In more preferred embodiments, the LPCs have formula (IId), where Z is $C_{1-12}$, preferably $C_{2-12}$, more preferably $C_{3-12}$, particularly $C_{4-12}$, most preferably $C_{6-12}$, $C_{7-12}$ or $C_{8-12}$ alkylene; t is 1; and $X^1$ is selected from halide, preferably chloride, OH, SH, $NH_2$, $COR^5$ and $COOR^4$, where $R^4$ is hydrogen, alkyl, aryl or aralkyl and $R^5$ is halide, heteroaryl or pseudohalide.

In particularly preferred embodiments, the LPCs have formula (IId), where Z is $C_{3-12}$, particularly $C_{4-12}$, most preferably $C_{6-12}$, $C_{7-12}$ or $C_{8-12}$ alkylene; t is 1; and $X^1$ is selected from halide, preferably chloride, OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is halide or $COR^5$ or $COOR^4$, preferably chloride or $COOR^4$.

In other particularly preferred embodiments, the LPCs have formula (IId), where Z contains 0, 1 or 2 methylene groups, preferably 0 (i.e., Z is absent); t is preferably 0; and $X^1$ is selected from halide, preferably chloride, OH, SH, $NH_2$, $COR^5$ and $COOR^4$, where $R^4$ is hydrogen, alkyl, aryl or aralkyl and $R^5$ is halide, heteroaryl, aryl or pseudohalide. In more preferred embodiments, $X^1$ is halide, $COR^5$ or $COOR^4$, preferably chloride or $COOR^4$. The presently most preferred LPCs of formula (IId) are 1,3,5-benzenetricarboxylic acid and 1,3,5-tri(chloromethyl)benzene.

In certain embodiments, the LPCs of formulae (IIc) and (IId) are chosen as above, with the proviso that Z contains more than two methylene groups. In other embodiments, the LPCs are chosen with the proviso that Z is not 1,4-arylene. In other preferred embodiments, the LPCs are chosen with the proviso that Z contains more than two methylene groups and is not 1,4-arylene. In other more preferred embodiments, the LPCs are chosen with the proviso that Z contains at least one, preferably at least two, more preferably three or more phenylene or methylene units.

b. Cyclic Multifunctional LPCs of Formulae (Ie) and (If)

In other more preferred embodiments, the LPCs have formulae (Ie) or (If):

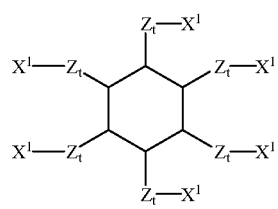
(Ie)

-continued

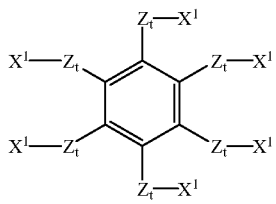
(If)

where Z is any combination of alklyene or arylene units as described above, of 0–12 units, preferably 1–12, more preferably 2–12, particularly 3–12, more particularly 4–12, most preferably 6–12, 7–12 or 8–12 units preferably selected from 1,4-phenylene and methylene, which units may be combined in any order; t is 0 or 1; $X^1$ is any reactive group which can be used in biopolymer synthesis (see, e.g., U.S. Pat. No. 5,198,540, the disclosure of which is incorporated herein by reference), and is preferably OH, SH, $NH_2$, $COR^5$ or $COOR^4$; n is 3 or 4; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In other preferred embodiments, the LPCs are of formula (Ie) where Z is any combination of 0–12, preferably 1–12, more preferably 2–12, particularly 3–12, more particularly 4–12, most preferably 6–12, 7–12 or 8–12, units selected from 1,4-phenylene and methylene, which units may be combined in any order; t is 0 or 1; $X^1$ is any reactive group which can be used in biopolymer synthesis (see, e.g., U.S. Pat. No. 5,198,540, the disclosure of which is incorporated herein by reference), and is preferably OH, SH, $NH_2$, $COR^5$ or $COOR^4$; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In more preferred embodiments, the LPCs have formula (Ie), where Z is $C_{1-12}$, preferably $C_{2-12}$, more preferably $C_{3-12}$, particularly $C_{4-12}$, most preferably $C_{6-12}$, $C_{7-12}$ or $C_{8-12}$ alkylene; t is 1; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide.

In particularly preferred embodiments, the LPCs have formula (Ie), where Z is $C_{3-12}$, particularly $C_{4-12}$, most preferably $C_{6-12}$, $C_{7-12}$ or $C_{8-12}$ alkylene; t is 1; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is $COR^5$ or $COOR^4$, preferably $COOR^4$.

In other particularly preferred embodiments, the LPCs have formula (Ie), where Z contains 0, 1 or 2 methylene units, preferably 0; t is preferably 0; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is $COR^5$ or $COOR^4$, preferably $COOR^4$, most preferably COOH.

In other preferred embodiments, the LPCs are of formula (If) where Z is any combination of 0–12, preferably 1–12, more preferably 2–12, particularly 3–12, more particularly 4–12, most preferably 6–12, 7–12 or 8–12, units selected from 1,4-phenylene and methylene, which units may be combined in any order; t is 0 or 1; $X^1$ is any reactive group which can be used in biopolymer synthesis (see, e.g., U.S. Pat. No. 5,198,540, the disclosure of which is incorporated herein by reference), and is preferably OH, SH, $NH_2$, $COR^5$ or $COOR^4$; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In more preferred embodiments, the LPCs have formula (If), where Z is $C_{1-12}$, preferably $C_{2-12}$, more preferably $C_{3-12}$, particularly $C_{4-12}$, most preferably $C_{6-12}$, $C_{7-12}$ or $C_{8-12}$ alkylene; t is 1; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide.

In particularly preferred embodiments, the LPCs have formula (If), where Z is $C_{3-12}$, particularly $C_{4-12}$, most preferably $C_{6-12}$, $C_{7-12}$ or $C_{8-12}$ alkylene; t is 1; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is $COR^5$ or $COOR^4$, preferably $COOR^4$.

In other particularly preferred embodiments, the LPCs have formula (If), where Z contains 0, 1 or 2 methylene groups, preferably 0 (i.e., Z is absent); t is preferably 0; and $X^1$ is selected from OH, SH, $NH_2$, $COR^5$ and $COOR^4$, where $R^4$ is hydrogen, alkyl, aryl or aralkyl and $R^5$ is halide, heteroaryl, aryl or pseudohalide. In more preferred embodiments, $X^1$ is $COR^5$ or $COOR^4$, preferably $COOR^4$, most preferably COOH.

In certain embodiments, the LPCs of formulae (Ie) and (If) are chosen as above, with the proviso that Z contains more than two methylene groups. In other embodiments, the LPCs are chosen with the proviso that Z is not 1,4-arylene. In other preferred embodiments, the LPCs are chosen with the proviso that Z contains more than two methylene groups and is not 1,4-arylene. In other more preferred embodiments, the LPCs are chosen with the proviso that Z contains at least one, preferably at least two, more preferably three or more phenylene or methylene units.

3. Dimeric LPCs

In preferred embodiments, the LPCs are composed of two of the groups of formula (I). The LPCs of this embodiment are symmetrical compounds such that all of the $X^1$ groups are equivalent. In more preferred embodiments, the LPCs have formulae:

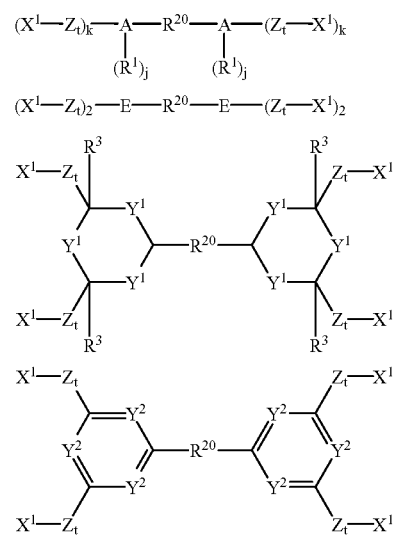

where A is carbon; E is nitrogen; $R^1$ and $R^3$ are each independently hydrogen, alkyl, aryl, aralkyl, heteroaryl, heteroaralkyl, heterocyclyl or heterocyclylalkyl; p is 0 or 1; Z as defined above is any combination of 0–12 units, preferably 1–12, more preferably 2–12, particularly 3–12, more particularly 4–12, most preferably 6–12, 7–12 or 8–12 units selected from 1,4-phenylene and methylene, which units may be combined in any order; $R^{20}$ is alkylene; t is 0 or 1; $X^1$ is any reactive group which can be used in biopolymer synthesis (see, e.g., U.S. Pat. No. 5,198,540, the disclosure of which is incorporated herein by reference), and is preferably OH, SH, $NH_2$, $COR^5$ or $COOR^4$; n is 3 or 4; $R^4$ is selected from hydrogen, alkyl, aryl, aralkyl, heteroaryl, heteroaralkyl, heterocyclyl and heterocyclylalkyl; $R^5$ is halide, heteroaryl or pseudohalide; $Y^1$ is $CH_2$, NH, S or O; and $Y^2$ is selected from CH and N.

In more preferred embodiments, $Y^1$ is $CH_2$ and $Y^2$ is CH.

Any of the groups $R^1$, $R^3$, $R^4$, $R^5$, $X^1$, $Y^1$, $Y^2$ and Z may be unsubstituted or substituted with one or more substituents each independently selected from Q.

In other preferred embodiments, the LPCs are of the above formulae where Z is any combination of 0–12, preferably 1–12, more preferably 2–12, particularly 3–12, more particularly 4–12, most preferably 6–12, 7–12 or 8–12, units selected from 1,4-phenylene and methylene, which units may be combined in any order; t is 0 or 1; $R^{20}$ is $C_{1-12}$, preferably $C_{1-6}$, alkylene; $X^1$ is any reactive group which can be used in biopolymer synthesis (see, e.g., U.S. Pat. No. 5,198,540, the disclosure of which is incorporated herein by reference), and is preferably halide, OH, SH, $NH_2$, $COR^5$ or $COOR^4$; $R^4$ is selected from hydrogen, alkyl, aryl, aralkyl, heteroaryl, heteroaralkyl, heterocyclyl and heterocyclylalkyl; and $R^5$ is halide, heteroaryl or pseudohalide.

In more preferred embodiments, the LPCs have the above formulae, where Z is $C_{1-12}$, preferably $C_{2-12}$, more preferably $C_{3-12}$, particularly $C_{4-12}$, most preferably $C_{6-12}$, $C_{7-12}$ or $C_{8-12}$ alkylene; t is 1; $R^{20}$ is lower alkylene; and $X^1$ is selected from halide, OH, SH, $NH_2$, $COR^5$ and $COOR^4$, where $R^4$ is hydrogen, alkyl, aryl or aralkyl and $R^5$ is halide, heteroaryl or pseudohalide.

In particularly preferred embodiments, the LPCs have the above formulae, where Z is $C_{3-12}$, particularly $C_{4-12}$, most preferably $C_{6-12}$, $C_{7-12}$ or $C_{8-12}$ alkylene; t is 1; $R^{20}$ is lower alkylene; and $X^1$ is selected from OH, SH, $NH_2$, $COR^5$ and $COOR^4$, where $R^4$ is hydrogen, alkyl, aryl or aralkyl and $R^5$ is halide, heteroaryl or pseudohalide. In more preferred embodiments, $X^1$ is $COR^5$ or $COOR^4$, preferably $COOR^4$.

In other particularly preferred embodiments, the LPCs have formula (IId), where Z contains 0, 1 or 2 methylene groups, preferably 0 (i.e., Z is absent) or 1; t is 0 or 1; $R^{20}$ is lower alkylene; and $X^1$ is selected from halide, preferably chloride, OH, SH, $NH_2$, $COR^5$ and $COOR^4$, where $R^4$ is hydrogen, alkyl, aryl or aralkyl and $R^5$ is halide, heteroaryl, aryl or pseudohalide. In more preferred embodiments, $X^1$ is halide, $COR^5$ or $COOR^4$, preferably chloride or $COOR^4$, most preferably chloride or COOH.

Most preferred compounds of the above formulae include:

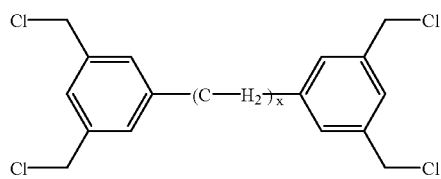

-continued

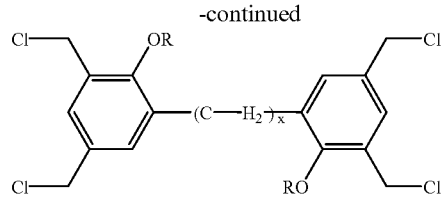

where x is 0–6 and R is lower alkyl

4. LPC Derivatives

In certain embodiments, it is desirable to modify the LPC prior to biopolymer synthesis. Such modification produces an LPC that has desirable physical characteristics, such as solubility or compatibility with chromatography, for biopolymer synthesis. The type of modification to be performed will depend on the nature of the biopolymer to be prepared.

a. LPCs for Oligonucleotide Synthesis

LPCs for use in oligonucleotide synthesis will preferably possess a carboxylic acid group or a derivative thereof at the terminus of $X^1$. This type of functionality may be used to form an ester linkage to, for example, the 3'-OH group of a first nucleotide or nucleoside monomer.

If $X^1$ is OH or SH, the modification involves reaction with, for example, acrylonitrile, followed by alcoholysis of the nitrile and reaction of the resulting ester with an α,ω-diamine, to form an amino derivative, for example, of the general formula $Sp(O,S-(CH_2)_2-C(O)-NH-(CH_2)_x-NH_2)_n$ where x is 0–6, preferably 1–4, more preferably 2. The presently most preferred LPC of this formula is tetrakis (8-amino-6-aza-2-oxa-5-oxooctyl)methane. The amine may then be further derivatized by reaction with, for example, an α,ω-alkanedioic acid anhydride to provide a compound of formula $Sp(O,S-(CH_2)_2-C(O)-NH-(CH_2)_x-NH-C(O)-(CH_2)_x-COOH)_n$, where x is 0–6, preferably 1–4, more preferably 2. The presently most preferred LPC of this formula is tetrakis(11-carboxy-6,9-diaza-5,10-dioxo-2-oxaundecyl)methane.

In embodiments where $X^1$ is $NH_2$, the LPC may be derivatized by reaction with, for example, an α,ω-alkanedioic acid anhydride to provide a compound of formula $Sp(NH-C(O)-(CH_2)_x-COOH)_n$, where x is 0–6, preferably 1–4, more preferably 2. The presently most preferred LPC of this formula is tris(3-aza-6-carboxy-4-oxohexyl)amine.

In embodiments where $X^1$ is $COOR^4$ or $COR^5$, the LPC may be derivatized by reaction with, for example, an α,ω-alkylenediamine, to form an amino derivative, for example, of the general formula $Sp(C(O)-NH-(CH_2)_x-NH_2)_n$ where x is 0–6, preferably 1–4, more preferably 2. The presently most preferred LPC of this formula is 1,3,5-benzenetricarboxylic acid tris-N-(2-aminoethyl)amide. The amine may then be further derivatized by reaction with, for example, an α,ω-alkanedioic acid anhydride to provide a compound of formula $Sp(C(O)-NH-(CH_2)_x-NH-C(O)-(CH_2)_x-COOH)_n$, where x is 0–6, preferably 1–4, more preferably 2. The presently most preferred LPC of this formula is 1,3,5-benzenetricarboxylic acid tris-N-(3-aza-6-carboxy-4-oxohexyl)amide.

In other more preferred embodiments, the carboxyl derivatives of formulae $Sp(O,S-(CH_2)_2-C(O)-NH-(CH_2)_x-NH-C(O)-(CH_2)_x-COOH)_n$, $Sp(NH-C(O)-(CH_2)_x-COOH)_n$ and $Sp(C(O)-NH-(CH_2)_x-NH-C(O)-(CH_2)_x-COOH)_n$ may be further derivatized by reaction with a first monomer unit for synthesis of a biopolymer. As exemplified herein, a first monomer unit in the synthesis of oligonucleotides may be 5'-O-dimethoxytrityl-2'-deoxythymidine or 2'-deoxythymidine. Preferred LPCs of this embodiment include tetrakis{6,9-diaza-13-[5'-O-(4,4'-dimethoxytriphenylmethyl)-2'-deoxythymidine-3'-O-yl]-2-oxa-5,10,13-trioxotridecyl}methane ((DMT-dT)$_4$-PE-LPC), 1,3,5-tris{2,5-diaza-9-[5'-O-(4,4'-dimethoxytriphenyl-methyl)-2'-deoxythymidine-3'-O-yl]-1,6,9-trioxononyl}-benzene ((DMT-dT)$_3$-Aryl-LPC), tetrakis[13-(2'-deoxythymidin-3'-O-yl)-6,9-diaza-2-oxa-5,10,13-trioxotridecyl]-methane (dT$_4$-PE-LPC), 1,3,5-tris[9-(2'-deoxythymidin-3'-O-yl)-2,5-diaza-1,6,9-trioxononyl]-benzene (dT$_3$-Aryl-LPC), tris-{3-aza-4,7-dioxo-7-[5'-O-(4,4'-dimethoxytriphenylmethyl)-2'-deoxythymidine-3'-O-yl]-heptyl}-amine ((DMT-dT)$_3$-Amine-LPC) and tris[3-aza-7-(2'-deoxythymidine-3'-O-yl)-4,7-dioxoheptyl]-amine (dT$_3$-Amine-LPC).

b. LPCs for Peptide Synthesis

LPCs for use in peptide synthesis will preferably possess a haloalkyl, hydroxyl, thio or carboxyl group at the terminus of $X^1$. The hydroxyl or thio groups may be used to form ester or thioester linkages to the carboxyl group of a first amino acid monomer. Preferred haloalkyl groups are benzylic halides that can form benzylic esters with the carboxyl terminus of a first monomer. The carboxyl group of $X^1$ may be used to form an amide linkage to the amino group of a first amino acid monomer. LPCs possessing carboxyl groups at the terminus of $X^1$ are described above.

In embodiments where $X^1$ is OH or SH, the modification involves reaction with, for example, acrylonitrile, followed by alcoholysis of the nitrile and reaction of the resulting ester with an α,ω-diol, dithiol or oxy-thiol, to form a hydroxy or thio derivative, for example, of the general formula $Sp(O,S—(CH_2)_2—C(O)—O,S—(CH_2)_x—OH,SH)_n$, where x is 0–6, preferably 1–4, more preferably 2.

In embodiments where $X^1$ is $NH_2$, the LPC may be derivatized by reaction with, for example, an α,ω-alkanedioic acid anhydride to provide a compound of formula $Sp(NH—C(O)—(CH_2)_x—COOH)_n$, where x is 0–6, preferably 1–4, more preferably 2. Reaction of the resulting acid with an α,ω-diol, dithiol or oxy-thiol, forms a hydroxy or thio derivative, for example, of the general formula $Sp(NH—C(O)—(CH_2)_x—CO—O,S—(CH_2)_x—OH,SH)_n$, where x is 0–6, preferably 1–4, more preferably 2.

In embodiments where $X^1$ is $COOR^4$ or $COR^5$, the LPC may be derivatized by reaction with, for example, an α,ω-diol, dithiol or oxy-thiol, to form a hydroxy or thio derivative, for example, of the general formula $Sp(C(O)—O,S—(CH_2)_x—OH,SH)_n$, where x is 0–6, preferably 1–4, more preferably 2.

In other more preferred embodiments, the hydroxy or thio derivatives of formulae $Sp(O,S—(CH_2)_2—C(O)—O,S—(CH_2)_x—OH,SH)_n$, $Sp(NH—C(O)—(CH_2)_x—CO—O,S—(CH_2)_x—OH,SH)_n$ or $Sp(C(O)—O,S—(CH_2)_x—OH,SH)_n$ may be further derivatized by reaction with a first monomer unit for synthesis of a biopolymer.

c. LPCs for Peptide Nucleic Acid (PNA) Synthesis

LPCs for use in PNA synthesis will preferably possess a haloalkyl, hydroxyl, thio or carboxyl group at the terminus of $X^1$. The hydroxyl or thio groups may be used to form ester or thioester linkages to the carboxyl group of a first PNA monomer. Preferred haloalkyl groups are benzylic halides that can form benzylic esters with the carboxyl terminus of a first monomer. The carboxyl group of $X^1$ may be used to form an amide linkage to the amino group of a first PNA monomer. LPCs possessing these groups at the terminus of $X^1$ are described above.

d. LPCs for Oligosaccharide Synthesis

LPCs for use in oligosaccharide synthesis will preferably possess a hydroxyl, thio or carboxyl group at the terminus of $X^1$. The hydroxyl or thio groups may be used to form glycosyl linkages to the a first saccharide monomer. The carboxyl group may be used to form an ester linkage to a hydroxyl (e.g., the 5- or 6-hydroxyl) group of a first saccharide monomer. LPCs possessing these groups at the terminus of $X^1$ are described above.

e. LPCs Coupled to Linkers

Alternatively, or in conjunction with the modifications described above, the LPC may be coupled with any linker known to those of skill in the art for use in biopolymer synthesis. Such linkers have traditionally been used in solid phase synthesis of biopolymers. The linkers include photocleavable, traceless, safety-catch or other linkers well known to those of skill in the art. See, e.g., Leznoff et al. *Can. J. Chem.* 1972, 50, 2892–2893; Frechet et al. *Can. J. Chem.* 1976, 54, 926–934; Chan et al. *J. Chem. Soc., Chem. Commun.* 1995, 1475–1476; Krchnak et al. *Mol. Divers.* 1995, 1, 149–164; Burgess et al. *J. Org. Chem.* 1997, 62, 5165–5168; Plunkett et al. *J. Org. Chem.* 1995, 60, 6006–6007; Han et al. *Tetrahedron Lett.* 1996, 37, 2703–2706; Lorsbach et al. *J. Org. Chem.* 1996, 61, 8716–8717; Newlander et al. *J. Org. Chem.* 1997, 62, 6726–6732; Worster et al. *Angew. Chem. Int. Ed. Eng.* 1979, 18, 221–222; Allin et al. *Tetrahedron Lett.* 1996, 37, 8023–8026; Lloyd-Williams et al. *Tetrahedron* 1993, 49, 11065–11133; Brown et al. *Mol. Divers.* 1995, 1, 4–12; Salmon et al. *Proc. Natl. Acad. Sci. U.S.A.* 1993, 90, 11708–11712; Cardno et al. *Tetrahedron Lett.* 1996, 37, 135–138; Kaldor et al. *Tetrahedron Lett.* 1996, 37, 7193–7196; DeGrado et al. *J. Org. Chem.* 1980, 45, 1295–1300; Bhargava et al. *J. Am. Chem. Soc.* 1983, 105, 3247–3251; Van Maarseveen et al. *Tetrahedron Lett.* 1996, 37, 8249–8252; Entwistle et al. *Tetrahedron Lett.* 1979, 555–558; Maeji et al. *J. Immunol. Meth.* 1990, 134, 23–33; Bray et al. *J. Org. Chem.* 1991, 56, 6659–6666; Backes et al. *J. Am. Chem. Soc.* 1996, 118, 3055–3056; Gayo et al. *Tetrahedron Lett.* 1997, 38, 211–214; Morphy et al. *Tetrahedron Lett.* 1996, 37, 3209–3212, Patek et al. *Tetrahedron Lett.* 1991, 32, 3891–3894; Routledge et al. *Tetrahedron Lett.* 1997, 38, 1227–1230; Fattom et al. (1992) *Infection & Immun.* 60:584–589; Goldmacher et al. (1992) *Bioconj. Chem.* 3: 104–107; Hazum et al. (1981) in *Pept., Proc. Eur. Pept. Symp.*, 16th, Brunfeldt, K (Ed), pp. 105–110; Yen et al. (1989) *Makromol. Chem* 190:69–82; Senter et al. (1985) *Photochem, Photobiol* 42:231–237 and U.S. Pat. Nos. 5,547,835, 5,635,598, 5,492,821, 5,652,358, 5,552,471, 5,736,626, 5,639,633, 5,736,625, 5,679,773, 5,648,462, 5,616,698 and 5,552,535. The disclosure of these references is herein incorporated by reference.

B. Preparation of Liquid Phase Carriers

The liquid phase carriers may be prepared by the methods described in detail herein, by minor modification of the methods or by other methods known to those of skill in the art. Certain of the LPCs described herein are commercially available from, for example, Aldrich Chemical Co., Milwaukee, Wis.

1. Preparation of LPCs of Formula (Ia)

Preparation of LPCs of formula (Ia) is exemplified by the syntheses of tetrakis{6,9-diaza-13-[5'-O-(4,4'-dimethoxytriphenylmethyl)-2'-deoxythymidine-3'-O-yl]-2-oxa-5,10, 13-trioxotridecyl}methane ((DMT-dT)$_4$-PE-LPC) and tetrakis[13-(2'-deoxythymidin-3'-O-yl)-6,9-diaza-2-oxa-5,10,13-trioxotridecyl]-methane (dT$_4$-PE-LPC), shown below (see also, Examples 1 and 3). Other LPCs of formula (Ia) may be prepared by minor modification of this method.
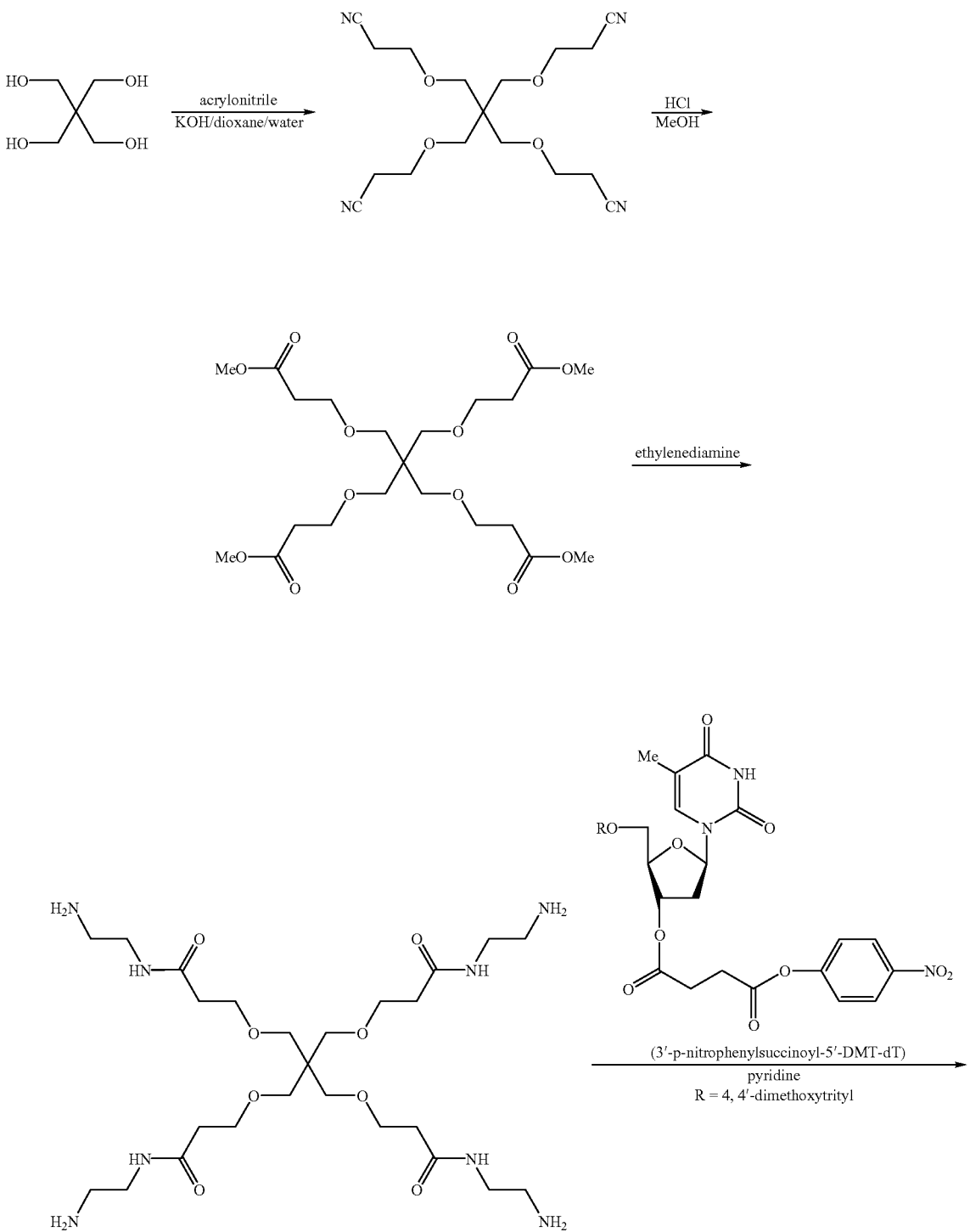

-continued

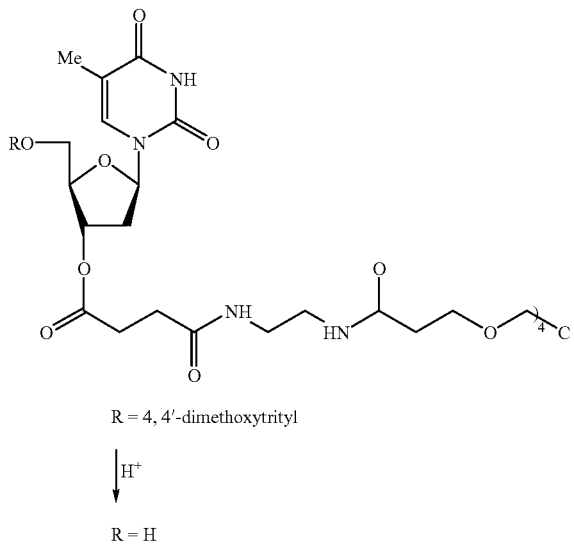

R = 4,4'-dimethoxytrityl

↓ H⁺

R = H

Treatment of pentaerythritol with acrylonitrile in the presence of KOH gave tetrakis-[(cyanoethoxy)methyl]methane. When refluxed with HCl saturated methanol under exclusion of water the nitrile reacts to form tetrakis-[((methoxy-carbonyl)ethoxy)methyl]methane. See, G. R. Newkome et al. *Aldrichim. Acta* 1992, 25, 31–38; G. R. Newkome et al. *Macromolecules* 1991, 24, 1443–1444 and G. R. Newkome et al. *Tetrahedron: Asymmetry*, 1991, 2, 957–960. Aminolysis with ethylendiamine leads to the tetravalent amine, tetrakis-(8-amino-6-aza-2-oxa-5-oxooctyl)-methane. See, A. D. Meltzer et al. *Macromolecules* 1992, 25, 4541–4548. The four primary amino functions were then acylated by the reactive p-nitrophenylester of 5'-O-dimethoxytrityl-deoxythymidine-3'-O-succinate in pyridine, leading to the highly symmetrical compound tetrakis-{6,9-diaza-13-[5'-O-(4,4'-dimethoxytriphenylmethyl)-2'-deoxythymidine-3'-O-yl]-2-oxa-5,10,13-trioxotridecyl}methane ((DMT-dT)$_4$-PE-LPC). Repeated low pressure liquid chromatography on silica gel and gel permeation chromatography (GPC) on Sephadex LH20 afforded pure material in a yield of 45%.

The next step, the dedimethoxytritylation of the LPC is the first necessary reaction for starting the synthesis of oligonucleotides and is also repeated at the beginning of every following cycle. An important aspect of this procedure is that the deprotection of the terminal 5'-hydroxyl group be rapid and complete. Long reaction times under acidic conditions will favor another known side reaction, the depurination of guanosine and adenosine units in the growing oligonucleotide chain.

In one method, cationic ion exchanger resins in their protonated form (Fractogel® EMD-SO$_3^-$ 650 (M) in H⁺-form) may be used for combined dedimethoxytritylation and purification by stepwise variation of the polarity of the solvent system (solid phase extraction). Nonpolar solvents (dichloromethane/ethanol mixtures) enable the fast separation of the dimethoxytrityl group with high flow rates. The 5'-O-deprotected LPC is eluted next with polar solvent systems such as ethanol or THF/ethanol mixtures. The yield of dT$_4$-PE-LPC was 93%.

In another method, dedimethoxytritylation with TFA (2%) in 1,2-dichloroethane/nitromethane/methanol 80:19:1 (v/v) was used for rapid cleavage of the 5'-O-protecting group, completed in less than 5 minutes. After neutralization (with, for example, triethylamine), purification may be performed with different types of chromatography media:

a) by solid phase extraction using LiChroprep® DIOL, or
b) by GPC using Sephadex LH20 and additional extraction of remaining dimethoxytritylcarbinol with diethyl ether, or
c) neutralization with n-trioctylamine, purification by reversed phase chromatography using NUCLEOPREP® 300-30 C18 (eluant: acetonitrile/THF/water 56:14:30 v/v), or
d) by reversed phase chromatography using NUCLEOPREP® 300-30 C18 in combination with gel permeation chromatography using Sephadex LH20 eluant: THF/water 70:30 v/v.

The use of water in these methods makes intensive drying of nucleotidic products necessary before the following coupling reaction with phosphoramidites is started. In general water is not necessary eluent for chromatography using only Sephadex LH20. Only a few very polar solvents are able to fulfill the demands for good solubility of all components and for other properties in this chromatography (sufficient swelling of Sephadex LH20, low viscosity, low boiling points for easy removal after GPC). Pyridine is preferred for this purpose, also because this solvent proved compatible with the condensation reaction with phosphoramidites for chain elongation, in contrast to water, alcohols, organic acids or strong bases.

2. Preparation of LPCs of Formula (Ib)

Preparation of LPCs of formula (Ib) is exemplified by the synthesis of tris-{3-aza-4,7-dioxo-7-[5'-O-(4,4'-dimethoxytriphenylmethyl)-2'-deoxythymidine-3'-O-yl]-heptyl}-amine ((DMT-dT)$_3$-Amine-LPC) and tris-[3-aza-7-(2'-deoxythymidine-3'-O-yl)-4,7-dioxoheptyl]-amine (dT$_3$-Amine-LPC), shown below (see also, Examples 5 and 6). Other LPCs of formula (Ib) may be prepared by minor modification of this method.

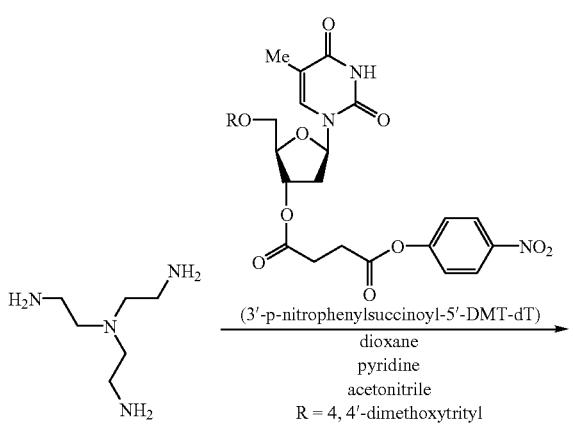

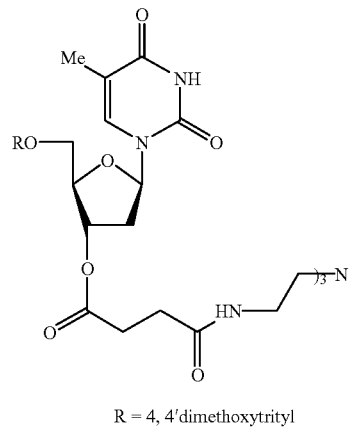

R = 4, 4'dimethoxytrityl

 H$^+$

R = H

This LPC may be prepared by minor modification of the method described above for synthesis of LPCs of formula (Ia). Synthesis starting with tris(2-aminoethyl)amine provided (DMT-dT)$_3$-Amine-LPC in good yield (74%). Dedimethoxytritylation under conditions described for LPCs of formula (Ia) gave dT$_3$-Amine-LPC.

3. Preparation of LPCs of Formulae (Ic) and (Id)

Preparation of LPCs of formulae (Ic) and (Id) are exemplified by the synthesis of 1,3,5-tris-{2,5-diaza-9-[5'-O-(4,4'-dimethoxytriphenylmethyl)-2'-deoxythymidine-3'-O-yl]-1,6,9-trioxononyl}-benzene ((DMT-dT)$_3$-Aryl-LPC) and 1,3,5-tris-[9-(2'-deoxythymidin-3'-O-yl)-2,5-diaza-1,6,9-trioxononyl]-benzene (dT$_3$-Aryl-LPC), shown below (see also, Examples 2 and 4). Other LPCs of formulae (Ic) and (Id) may be prepared by minor modification of this method.

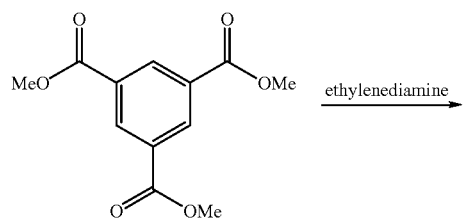

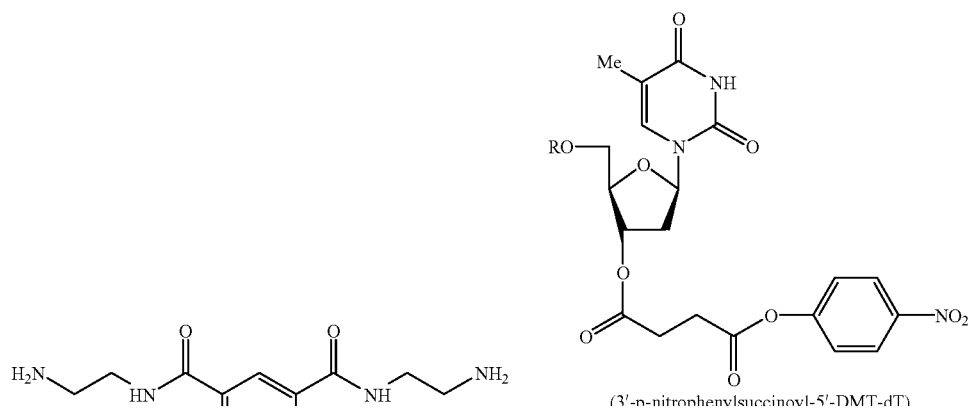

-continued

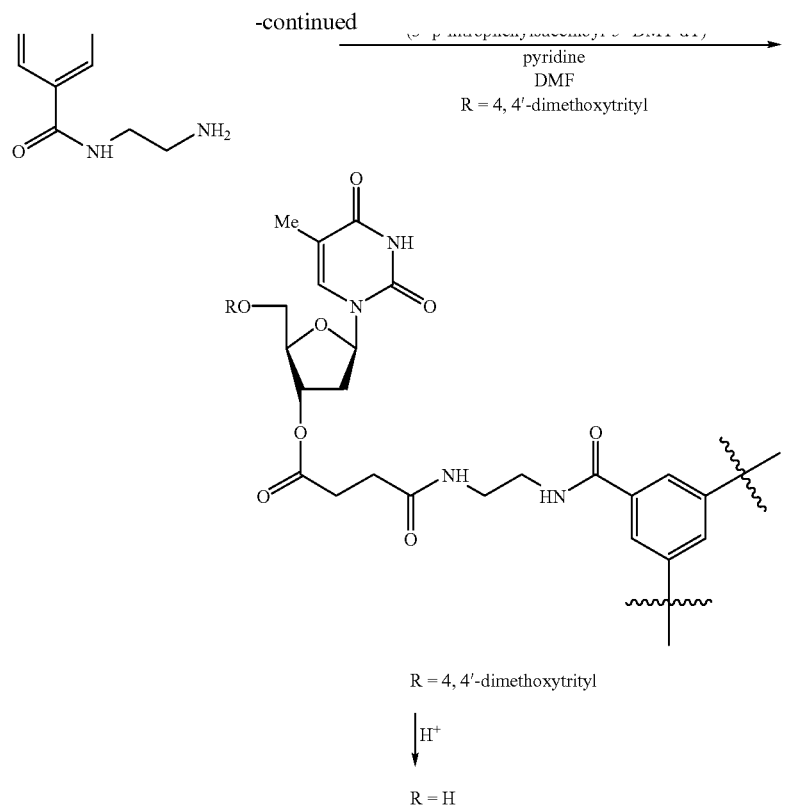

R = 4, 4'-dimethoxytrityl

↓ H⁺

R = H

Aminolysis of commercially available 1,3,5-benzene tricarboxylic acid trimethyl ester using ethylenediamine gave the triamide shown. This triamide, 1,3,5-benzene tricarboxylic acid tris-N-(2-aminoethyl)amide, was then treated with the p-nitrophenylester of 5'-O-dimethoxytrityl-deoxythymidine-3'-O-succinate in pyridine/DMF to give an aryl type liquid phase carrier, abbreviated as (DMT-dT)$_3$-Aryl-LPC, in yields of up to 90%. Silica gel column chromatography and GPC on Sephadex LH20 were used for purification, $^1$H- and $^{13}$C-NMR for identification.

C. Methods of Solution Phase Biopolymer Synthesis

Methods of synthesis of biopolymers using the LPCs described herein are also provided. Relatively large amounts of biopolymers, including, but not limited to, oligonucleotides, peptides, PNAs and oligosaccharides, may be produced by the methods. It is possible to prepare not only naturally occurring biopolymers, but also analogs of the biopolymers. Such analogs include, for example, analogs of oligonucleotides such as oligo-triesters or oligophosphonates. Use of the LPCs provided herein in the methods provided afford biopolymers of high purity and in significantly higher yields than methods known in the art.

In one embodiment, the methods involve the steps of (a) reacting an LPC of formula $Sp(X^1)_n$, provided herein, with a first monomer $N^1$; (b) separating and purifying the product of step (a) to afford a compound of formula $Sp(X^1-N^1)_n$; (c) reacting the product of step (b) with a second monomer $N^2$, a dimer $N^2-N^3$ or trimer $N^2-N^3-N^4$; (d) repeating steps (b) and (c) using the desired monomers, dimers or trimers to produce the desired LPC-bound biopolymer of formula $Sp(X^1-N^1-N^2-\ldots-N^m)_n$, where m is 3 to 100, preferably 3–50, more preferably 3–30, most preferably 3–15 or 3–10; and (e) cleaving the biopolymer from the LPC.

In embodiments where the biopolymer is an oligonucleotide, peptide or a PNA, m is preferably 3–30, more preferably 3–15. In embodiments where the biopolymer is an oligosaccharide, m is preferably 3–15, more preferably 3–10.

The separation and purification steps may be accomplished by any method known to those of skill in the art. Preferred methods include gel permeation chromatography (GPC) and chromatography on reverse phase (RP) silica gel. In more preferred embodiments, combinations of GPC and RP-silica gel chromatography are used.

Cleavage of the biopolymer from the LPC is achieved through standard means and depends on the nature of the linkage between the LPC and the biopolymer. For example, ester linkages may be cleaved with a base, such as hydroxide, alkoxides and amines. In certain embodiments, ammonium hydroxide is preferred. In other embodiments, the linkages may be silyl or trityl ethers, or glycosyl bonds. In these embodiments, treatment with acid, such as acetic acid, will cleave the biopolymer from the LPC. In embodiments where a linker is used to couple the LPC to the biopolymer, the cleavage conditions will depend on the nature of the linker. For example, light of a specific wavelength can be used to release a biopolymer from a photocleavable linker.

1. Monomers, Dimers and Trimers

Monomers (N), dimers and trimers used in preparing the biopolymer will depend on the biopolymer desired. For example, monomers which are used in the methods include nucleotides, nucleosides, natural and unnatural amino acids, PNA monomers and monosaccharides. Dimers and trimers are composed of the monomers. The monomers are used or obtained in the course of synthesis in protected form; typical examples of such protective groups are well known to those of skill in the art (see, e.g., *Tetrahedron* 1981, 363–369; *Liebigs Ann. Chem.* 1978, 839–853; *Nucleic Acids Research, Symposium Series No. 7* 1980, 39–59; and T. W. Greene *Protective groups in Organic Synthesis* (John Wiley & Sons, Inc., 1981)).

2. Biopolymeric Synthetic Protocols

In the methods, synthesis of the biopolymeric chain (i.e., steps c and d) may be carried out using any protocols known to those of skill in the art. For example, in the synthesis of oligonucleotides, the phosphate triester, phosphite triester, H-phosphonate or phosphoramidite protocols may be used. See, e.g., N. D. Sinha et al. *Tetrahedron Lett.* 1983, 24, 5843–5846; H. Köster et al. *Tetrahedron* 1984, 40, 103–112; N. D. Sinha et al. *Nucleic Acids Res.* 1984, 12, 4539–4557; S. L. Beaucage et al. *Tetrahedron* 1992, 48, 2223–2311; E. Sonveaux *Bioorg. Chem.* 1986, 14, 274–325; P. J. Garegg et al. *Tetrahedron Lett.* 1986, 27, 4051–4054; B. C. Froehler *Tetrahedron Lett.* 1986, 27, 5575–5578; B. C. Froehler et al. *Tetrahedron Lett.* 1986, 27, 469–472; S. L. Beaucage et al. *Tetrahedron Lett.* 1981, 22, 1859–1862; and U.S. Pat. Nos. 5,037,882, 5,616,700, 5,571,902, 5,705,621, 5,700,922, 5,610,289, 5,635,488, 5,668,266, 5,648,480 and 5,221,736. The H-phosphonate and phosphoramidite protocols are presently preferred. More preferred is the β-cyanoethyl phosphoramidite protocol.

For the synthesis of peptides, any protocols known to those of skill in the art may be used in the methods. For example, protocols such as those described in U.S. Pat. Nos. 5,726,243, 5,705,333, 4,749,742, 5,644,029, 5,637,719, 5,262,331, 4,794,150, 5,221,736 and 5,641,862 may be used.

For PNA synthesis, protocols such as those found in Brown et al. *Science* 1994, 265, 777–780; Norton et al. *Bioorg. & Med. Chem.* 1995, 3, 437–445; Schmidt et al. *Nucl. Acids Res.* 1997, 25, 4792–4796 and U.S. Pat. Nos. 5,700,922, 5,736,336, 5,719,262, 5,714,331, 5,705,333 and 5,539,083 may be used.

For oligosaccharide synthesis, protocols such as those found in U.S. Pat. Nos. 5,246,840, 5,616,698, 5,374,655, 5,288,637, 5,532,147 and 5,583,042 may be used.

All of the preceding publications and patents regarding protocols for biopolymer synthesis are incorporated by reference herein.

3. LPCs for use in the Methods

LPCs for use in the methods are any of those provided herein. The LPCs have the formula $Sp(X^1)_n$, wherein Sp is a polyvalent group that has two or more, preferably three or more, more preferably 3–6, points of attachment, n corresponds to the number of points of attachment in Sp and $X^1$ is a reactive group that is compatible from the point of view of biopolymer chemistry. Sp is preferably a symmetrical group such that all $X^1$ groups are equivalent. It will be appreciated by those of skill in the art that such symmetry allows for uniformity in the synthesis of n biopolymers using these LPCs.

In preferred embodiments, the LPCs used in the methods are of formulae (I) or derivatives thereof as described above, more preferably of formulae (Ia), (Ib) and (Id), or derivatives thereof. In more preferred embodiments, the LPCs used in the methods are of formulae (IIa), (IIb) or (IId), or derivatives thereof.

In particularly preferred embodiments of the methods, the LPCs are suitable for oligonucleotide synthesis. Such LPCs include the carboxyl derivatives of formulae (IIa), (IIb) or (IId) that have the general formulae $Sp(O,S-(CH_2)_2-C(O)-NH-(CH_2)_x-NH-C(O)-(CH_2)_x-COOH)_n$, $Sp(NH-C(O)-(CH_2)_x-COOH)_n$ and $Sp(C(O)-NH-(CH_2)_x-NH-C(O)-(CH_2)_x-COOH)_n$.

In other more preferred embodiments, the LPCs used in the methods are the carboxyl derivatives of formulae $Sp(O,S-(CH_2)_2-C(O)-NH-(CH_2)_x-NH-C(O)-(CH_2)_x-COOH)_n$, $Sp(NH-C(O)-(CH_2)_x-COOH)_n$ and $Sp(C(O)-NH-(CH_2)_x-NH-C(O)-(CH_2)_x-COOH)_n$ that are further derivatized by reaction with a first monomer unit for synthesis of a biopolymer, preferably an oligonucleotide. As exemplified herein, a first monomer unit in the synthesis of oligonucleotides may be 5'-O-dimethoxytrityl-2'-deoxythymidine or 2'-deoxythymidine. Preferred LPCs of this embodiment include tetrakis{6,9-diaza-13-[5'-O-(4,4'-dimethoxytriphenylmethyl)-2'-deoxythymidine-3'-O-yl]-2-oxa-5,10,13-trioxotridecyl}methane ((DMT-dT)$_4$-PE-LPC), 1,3,5-tris{2,5-diaza-9-[5'-O-(4,4'-dimethoxytriphenyl-methyl)-2'-deoxythymidine-3'-O-yl]-1,6,9-trioxononyl}-benzene ((DMT-dT)$_3$-Aryl-LPC), tetrakis[13-(2'-deoxythymidin-3'-O-yl)-6,9-diaza-2-oxa-5,10,13-trioxotridecyl]-methane (dT$_4$-PE-LPC), 1,3,5-tris[9-(2'-deoxythymidin-3'-O-yl)-2,5-diaza-1,6,9-trioxononyl]-benzene (dT$_3$-Aryl-LPC), tris-{3-aza-4,7-dioxo-7-[5'-O-(4,4'-dimethoxytriphenylmethyl)-2'-deoxythymidine-3'-O-yl]-heptyl}-amine ((DMT-dT)$_3$-Amine-LPC) and tris[3-aza-7-(2'-deoxythymidine-3'-O-yl)-4,7-dioxoheptyl]-amine (dT$_3$-Amine-LPC).

4. Preferred Embodiments of the Method

In a preferred embodiment, the method is used to prepare oligonucleotides. This is achieved through chain elongation in the 3'→5' direction with monomeric, dimeric or trimeric phosphoramidites. The procedure represents a way to a purification oriented and effective technique for the synthesis of oligonucleotides and their analogs in preparative scale. The purification, mainly achieved by gel permeation chromatography (GPC) on Sephadex LH20, is facilitated through the coupling of the intermediates to the LPC. The considerable difference in size between reaction products and all other reagents including the excess phosphoramidites allows separation by gel filtration. The condensation product, as the largest component, is eluted first near the void volume. Moreover the LPC mediates the solubility in organic solvents during the different reaction steps and the chromatography process.

Preferably after dedimethoxytritylation the reaction products can be analyzed by MALDI-TOF mass spectrometry. Through such analysis, a direct reaction control on the step of the fully base and phosphate protected intermediates is possible. The scale of synthesis is mainly determined by the dimension of the Sephadex LH20 column and can be varied in a wide range, including up to grams or kilograms.

In an exemplary embodiment, the method involves the synthesis of the decanucleotide d(GACGGCCAGT) using monomeric phosphoramidites and an LPC based on a 1,3,5-benzene tricarboxylic acid derivative (see, Example 7).

As described in detail in Example 7, the synthesis of decanucleotide d(GACGGCCAGT) was performed using the LPC 1,3,5-tris-[9-(2'-deoxythymidine-3'-O-yl)-2,5-diaza-1,6,9-trioxononyl]-benzene ((dT)$_3$-Aryl-LPC). Absolute pyridine was used in the condensation reactions. 166 μmol of the LPC (corresponds to 500 μmol 5'-hydroxyl groups) were dissolved in dry pyridine and together with a solution of 1H-tetrazole in acetonitrile added to 2.5 equivalents of the solid 5'-O-(DMT)-dG$^{ib}$-phosphoramidite under exclusion of moisture in an argon atmosphere. Phosphoramidite and tetrazole solution were added until no further reaction was observed; a total of 2 g (2.4 mmol, 5 eq.) 5'-O-(DMT)-dG$^{ib}$-phosphoramidite and 12 ml (5.2 mmol, 10 eq.) tetrazole solution were used. The condensation was monitored by thin layer chromatography (TLC). The resulting mixture of product and excess reagents including several equivalents of phosphoramidite was carefully reduced to a volume up to 10 ml and separated on a Sephadex LH20 column with THF/methanol 80:20 (v/v) as eluent. As expected, the condensation product eluted near the void volume, followed by the excess phosphoramidite components and finally the solvent, pyridine.

After GPC, the fractions containing the condensation product were combined and oxidized with t-butylhydroperoxide (t-BuOOH) at 0° C. The t-butylhydroperoxide (boiling point 81° C.) can easily be removed by co-evaporation with the solvents used in the oxidation (THF and methanol). The solution was reduced to dryness and the residue dissolved in dichloromethane/nitromethane/methanol 80:19:1 (v/v). For dedimethoxytritylation the resulting colorless solution was mixed with trifluoroacetic acid (TFA) in the same solvent system, so that a final acid concentration not higher than 2% (by volume) was obtained. The removal of the 5'-O-protecting group was complete in less than 2 minutes and indicated by a deep red to orange color. To avoid depurination the reaction was stopped by neutralization with triethylamine in an ice bath. For separation of the dedimethoxytritylated LPC compound Sephadex LH20 chromatography with a RP-silica gel filled precolumn (NUCLEOPREP® 300-30 $C_{18}$) was used. The precolumn was necessary to prevent contamination with dimethoxytrityl carbinol. In the first cycle the intermediate $d(G^{ib}T)_3$-Aryl-LPC was isolated as a colorless powder after drying by co-evaporation with dioxane. The identification by MALDI-TOF mass spectrometry showed no significant side products at that stage of synthesis.

The synthesis then followed the procedure described for the first cycle without essential changes of the method. Table 1 shows the yields, achieved in the nine cycles for condensation and oxidation (81–99%), dedimethoxytritylation (81–99%) and the whole cycle (81–99%). The total yield over all cycles amount to 33% for $d(5'-O-DMT-G^{ib}A^{bz}C^{bz}G^{ib}G^{ib}C^{bz}C^{bz}A^{bz}G^{ib}T)_3$-Aryl-LPC, including 26 reaction steps and 17 chromatographic separations. The quantities of reagents used in the synthesis are listed in Table 2 (see, Example 7). The used excess of β-cyanoethyl phosphoramidites varied between 5 and 12 equivalents, however, as little as 2 to 2.5 equivalents may be used. In this case the procedures for drying of the 5'-hydroxyl components were more intensive. Separation is in general quantitative. The average yield of 96% for the coupling reaction is comparable to that obtained with solid phase synthesis and better than comparable synthesis in solution. The average yield for dedimethoxytritylation is 87%. Preferred embodiments of the method avoid the use of water in chromatography. Other polar solvents for GPC on Sephadex LH20, such as pyridine or N,N-dimethylformamide, are favored for this purpose.

Table 1

Yields achieved in the oligonucleotide synthesis in solution using $dT_3$-Aryl-LPC for the preparation of decamer d(GACGGCCAGT)

TABLE 1

Yields achieved in the oligonucleotide synthesis in solution using $dT_3$-Aryl-LPC for the preparation of decamer d(GACGGCCAGT)
Synthesis of
$d(5'-O-DMT-G^{ib}A^{bz}C^{bz}G^{ib}G^{ib}C^{bz}C^{bz}A^{bz}G^{ib}T)_3$-Aryl-LPC, starting with 166 μmol $dT_3$-Aryl-LPC 1 [yields in % and μmol]:

| Cycle: | condensation: | dedimethoxy-tritylation: | yield per cycle: |
|---|---|---|---|
| 1 | 87%, 144 μmol using (DMT-dG$^{ib}$)-amidite | 94%, 135 μmol | 81% |
| 2 | 93%, 126 μmol using (DMT-dA$^{bz}$)-amidite | 87%, 110 μmol | 81% |
| 3 | 91%, 100 μmol using (DMT-dC$^{bz}$)-amidite | 99%, 100 μmol | 91% |
| 4 | 98%, 98 μmol using (DMT-dC$^{bz}$)-amidite | 86%, 84 μmol | 84% |
| 5 | 99%, 83 μmol using (DMT-dG$^{ib}$)-amidite | 96%, 80 μmol | 95% |
| 6 | 99%, 80 μmol using (DMT-dG$^{ib}$)-amidite | 81%, 65 μmol | 81% |
| 7 | 99%, 65 μmol using (DMT-dC$^{bz}$)-amidite | 83%, 54 μmol | 83% |
| 8 | 99%, 54 μmol using (DMT-dA$^{bz}$)-amidite | 99%, 54 μmol | 99% |
| 9 | 99%, 54 μmol using (DMT-dG$^{ib}$)-amidite | | |
| total: | 87–99%, Ø= 96% | 81–99%, Ø = 91% | 81–99%, Ø = 87% |

An inherent advantage of large scale oligonucleotide synthesis in solution in comparison to solid phase strategies is shown by the use of MALDI-TOF mass spectrometry for analysis of the fully base and phosphate protected intermediates. In contrast to solid phase synthesis, a direct control of the progressing elongation reaction is possible by analysis with this technique (for preparation of probes out of condensation, dedimethoxytritylation is necessary). For analysis of the condensation products from solid phase synthesis, cleavage of the connecting linker is necessary. The hydrolysis also leads to loss of phosphate and base protecting groups. Evidence about side reactions or incomplete reaction is therefore complicated in the analysis. The control over the basic elongation step in oligonucleotide synthesis is however of great importance for economic large scale production.

The analysis of product d(GACGGCCAGT), synthesized on $dT_3$-Aryl-LPC, was performed, after treatment with ammonium hydroxide, RP-HPLC and dedimethoxytritylation with acetic acid, by SMART-HPLC (Mono Q 16/5) and MALDI-TOF mass spectrometry.

In another exemplary embodiment, dimer phosphoramidites were used in the synthesis of the pentanucleotide d(GCCCT) (see, Example 8). Such building blocks are advantageous in oligonucleotide synthesis in solution because the number of coupling cycles and purification steps is reduced.

The preparation of an oligonucleotide of the sequence d(GCCCT), using the developed method for solution synthesis together with dimer phosphoramidites, demonstrated that these synthons are in general very useful. The phosphorylation is indicated by MALDI-TOF mass spectrometry through the detected fragment ion at 3306.4 m/z, corresponding to $d(5'-HO—C^{tl}C^{tl}T)_2(5'-pdT)$-Aryl-LPC (theoretical mass: 3272.9 Da). The steps in one elongation cycle are performed with no significant changes to that described for monomeric phosphoramidites. Instead of 1H-tetrazole the somewhat more activating 5-(4-nitrophenyl)-tetrazole is used. The coupling yield was 83%.

The following examples are included for illustrative purposes only and are not intended to limit the scope of the invention.

EXAMPLE 1

Tetrakis-{6,9-diaza-13-[5'-O-(4,4'-dimethoxytriphenylmethyl)-2'-deoxythymidine-3'-O-yl]-2-oxa-5,10,13-trioxotridecyl}methane ((DMT-dT)$_4$-PE-LPC)

A. Tetrakis-[(2-cyanoethoxy)methyl]methane

Pentaerythritol (6.84 g, 50 mmol) was dissolved in 20 ml dioxane and 2 ml water and mixed up with 40% aqueous potassium hydroxide solution (w/v, 1 ml). After cooling to 0° C. in an ice bath, acrylonitrile (16.2 g, 300 mmol) was added and the mixture stirred for 48 h at room temperature. Solvents were evaporated, the remaining oil was diluted in 100 ml dichloromethane and washed with 10% aqueous sodium chloride solution (w/v, 50 ml). After re-extraction of the aqueous layer with dichloromethane (2×25 ml), the combined organic layers were dried over sodium sulfate and intensively evaporated. The nitrile was obtained as a colorless syrup: yield: 14.32 g (41 mmol, 82%). $^1$H-NMR (400 MHz, CDCl$_3$) δ 2.60 (t, 8 H,—CH$_2$CN), 3.50 (s, 8 H, —C$_q$CH$_2$O—), 3.65 (t, 8 H, —OCH$_2$—). $^{13}$C-NMR (100 MHz, CDCl$_3$) δ 18.86 (—CH$_2$CN), 45.68 (C$_q$), 65.88 (—OCH$_2$—), 68.82 (C$_q$CH$_2$O—), 118.22 (CN).

B. Tetrakis-{[2-(methoxycarbonyl)ethoxy]methyl}-methane

Tetrakis-[(2-cyanoethoxy)methyl]-methane (3.48 g, 10 mmol) was dissolved in dried methanol (30 ml) and saturated with dried hydrogen chloride at room temperature. The reaction mixture was refluxed for 1 h under continuous passing of hydrogen chloride gas. During cooling to room temperature argon was passed through the whole apparatus. After hydrolysis with ice cold water, work up was performed (150 ml) through extraction with diethyl ether (3×100 ml) and drying of the combined organic layers with sodium sulfate. Intensive evaporation leads to the methyl ester as a yellowish oil: yield: 75% (3.72 g, 7.5 mmol). $^1$H-NMR (400 MHz, CDCl$_3$) δ 2.55 (t, 8 H, —CH$_2$CO—), 3.32 (s, 8 H, —C$_q$—CH$_2$O—), 3.65 (t, 8 H, —OCH$_2$—), 3.70 (s, 12 H, —OCH$_3$). $^{13}$C-NMR (100 MHz, CDCl$_3$) δ 34.92 (—CH$_2$CO—), 45.35 (C$_q$), 51.16 (CH$_3$), 66.60 (—OCH$_2$—), 69.23 (C$_q$CH$_2$O—), 172.14 (CO).

C. Tetrakis-(8-amino-6-aza-2-oxa-5-oxooctyl)-methane

The methyl ester from Example I.B. (3.91 g, 8 mmol) was dissolved in dried methanol (20 ml) and mixed up with a large excess of freshly distilled ethylenediamine (dried over CaH$_2$) at 0° C. (200 ml, 3 mol). Under inert atmosphere (argon) the solution was stirred for 96 h at 4° C. Ethylenediamine was removed by evaporation and co-evaporation after dissolving in methanol (10 ml) and addition of toluene (100 ml, 3 times): yield: 88% (4.01 g, 7 mmol). $^1$H-NMR (400 MHz, CDCl$_3$) δ 1.60 (br, 8 H, —NH$_2$), 2.40 (t, 8 H, —CH$_2$CO—), 2.82 (m, 8 H, —CH$_2$NH$_2$), 3.30 (m, 8 H, —NHCH$_2$—), 3.32 (s, 8 H, C$_q$CH$_2$O—), 3.68 (t, 8 H, —OCH$_2$—), 7.05 (m, 4 H, NH). $^{13}$C-NMR (100 MHz, CDCl$_3$) δ 36.94 (—CH$_2$CO—), 41.57 (—NHCH$_2$—), 42.34 (CH$_2$NH$_2$), 45.37 (C$_q$), 67.58 (—OCH$_2$—), 69.73 (C$_q$CH$_2$O—), 171.90 (CO).

D. Tetrakis-{6,9-diaza-13-[5'-O-(4,4'-dimethoxytriphenylmethyl)-2'-deoxythymidine-3'-O-yl]-2-oxa-5,10,13-trioxotridecyl}-methane ((DMT-dT)$_4$-PE-LPC)

The synthesis of 5'-O-dimethoxytrityl-deoxythymidine-3'-p-nitrophenylsuccinate was performed according to the procedure in *Oligonucleotide Synthesis, IRL Practical Approach Series*, Hrsg.: M. J. Gait, IRL-Press Ox ford (1984). The obtained solution in dioxane/pyridine, containing the p-nitrophenyl ester (approx. 5.4 mmol) was concentrated under reduced pressure and dissolved in pyridine (10 ml). Tetrakis-(8-amino-6-aza-2-oxa-5-oxooctyl)-methane (600 mg, 1 mmol) was added and stirred for 16 h at room temperature. Reaction mixture was concentrated and dissolved in eluent mix. The first chromatography on silica gel was performed using a step gradient from dichloromethane/ethanol 95:5 (v/v) to dichloromethane/ethanol 60:40 (v/v). All solvents contained 0.5% pyridine (v/v). Further purification with gel permeation chromatography on Sephadex LH20 gave only small portions of pure material (eluent: THF/isopropanol 80:20, v/v). Repeated silica gel column chromatography (with dichloromethane/ethanol, 15 to 30% ethanol, 0.5% pyridine) and gel permeation chromatography gave the product in colorless crystalline form, total yield: 45% (1.4 g, 0.45 mmol). $^1$H-NMR (400 MHz, CDCl$_3$) δ 1.37 (s, 12 H, CH$_3$—, Base), 2.40 (m, 8 H, —CH$_2$CO—), 2.40/2.50 (m, 8 H, H2'), 2.49 (m, 8 H, —COCH$_2$—), 2.63 (m, 8 H, —CH$_2$CO—), 3.29 (s, 8 H, C$_q$CH$_2$O), 3.36 (m, 16 H, 2×—NHCH$_2$—) 3.43 (m, 8 H, H5'), 3.68 (m, 8 H, —OCH$_2$—), 3.76 (s, 24 H; CH$_3$O—), 4.15 (m, 4 H, H4'), 5.43 (m, 4 H, H3'), 6.35 (dd, 4 H, H1'), 6.8–7.4 (m, 52 H, H$_{Ar}$), 7.60 (s, 4 H, CH, Base), 8.62 (dd, 2×4 H, 2×—NH—CH$_2$—), 9.90 (s, 4 H, NH, Base). $^{13}$C-NMR (100 MHz, CDCl$_3$) δ 11.63 (CH$_3$, Base), 29.74 (C12), 30.56 (C11), 36.79 (C4), 37.80 (C2'), 39.38 (C8), 40.01 (C7), 55.28 (—OCH$_3$), 63.85 (C5'), 67.50 (C3), 69.24 (C1), 75.88 (C3'), 83.81/84.30 (C1'/C4'), 87.22 (C$_Z$, DMT), 111.93 (C5, Base), 113.34 (C3, DMT), 127.26/128.06/128.13 (C2'/C3'/C4', DMT), 130.09 (C2, DMT), 135.09 (C1, DMT), 135.40 (C6, Base), 144.16 (C1', DMT), 151.34 (C2, Base), 158.75 (C4, DMT), 164.24 (C4, Base), 171.96 (C5 and C10), 172.16 (C13).

EXAMPLE 2

1,3,5-Tris-{2,5-diaza-9-[5'-O-(4,4'-dimethoxytriphenylmethyl)-2'-deoxythymidine-3'-O-yl]-1,6,9-trioxononyl}-benzene ((DMT-dT)$_3$-Aryl-LPC)

A. 1,3,5-Benzenetricarboxylic acid tris-N-(2-aminoethyl)amide 1,3,5-Benzenetricarboxylic acid trimethyl ester (1.04 g 4.0 mmol) was treated with ethylenediamine (66.7 ml, 1 mol), following the procedure described in Example 1.C. The reaction was complete after 24 h. After lyophilization with dioxane the product was obtained as a white solid; yield: 99% (1.35 g, 4.0 mmol). $^1$H-NMR (400 MHz, d$_6$-DMSO) δ 1.55 (br, 6 H, —NH$_2$), 2.72 (m, 6 H, —CH$_2$NH$_2$), 3.32 (m, 6 H, —NHCH$_2$—), 8.42 (s, 3 H, CH$_{Ar}$), 8.65 (t, 3 H, NH). $^{13}$C-NMR (100 MHz, d$_6$-DMSO) δ 42.16 (—CH$_2$NH$_2$), 44.16 (—NHCH$_2$—), 129.30 (CH$_{Ar}$), 135.95 (C$_{Ar}$), 166.56 (CO).

B. 1,3,5-Tris-{2,5-diaza-9-[5'-O-(4,4'-dimethoxytriphenylmethyl)-2'-deoxythymidine-3'-O-yl]-1,6,9-trioxononyl}-benzene ((DMT-dT)$_3$-Aryl-LPC)

A solution of 5'-O-dimethoxytrityl-deoxythymidine-3'-p-nitrophenylsuccinate (approx. 10 mmol) in dioxane/pyridine was concentrated under reduced pressure and dissolved in DMF (25 ml) and pyridine (10 ml). 1,3,5-Benzenetricarboxylic acid tris-N-(2-aminoethyl)amide (Example 2.B.) (673 mg, 2 mmol) was added, the reaction mixture stirred for 16 h at room temperature, concentrated and dissolved in eluent mix. Silica gel column chromatography (step gradient with dichloromethane and 2 to 20% ethanol, 0.5% pyridine, v/v) led to mostly pure product fractions. Gel permeation chromatography on Sephadex LH20 (eluent: THF/methanol 80:20 v/v) of the impure fractions gave additional product, total yield: 90% (4.0 g, 1.8 mmol). $^1$H-NMR (400 MHz, CDCl$_3$) δ 1.32 (s, 9 H, CH$_3$—, Base), 2.40/2.50 (m, 6 H, H2'), 2.44 (m, 6 H, —COCH$_2$—), 2.50 (m, 6 H, —CH$_2$CO—), 3.40 (m, 6 H, H5'), 3.54 (m, 12 H, 2×—NHCH$_2$—), 3.77 (s, 18 H, CH$_3$O—), 4.15 (m, 3 H, H4'), 5.40 (m, 3 H, H3'), 6.32 (dd, 3 H, H1'), 6.8–7.4 (m, 39 H, H$_{Ar}$), 7.60 (s, 3 H, CH, Base), 8.19 (dd, 2×3 H, 2×—NH—CH$_2$—), 8.40 (s, 3 H, CH$_{Ar}$). $^{13}$C-NMR (100 MHz, CDCl$_3$) δ 11.66 (CH$_3$, Base), 29.97 (C8), 30.66 (C7), 37.57 (C2'), 39.38 (C4), 40.57(C3), 55.26 (—OCH$_3$), 63.79 (C5'), 75.80 (C3'), 83.58/84.27 (C1'/C4'), 87.21 (C$_Z$, DMT), 112.06 (C5, Base), 113.34 (C3, DMT), 127.24/128.13/128.23 (C2'/C3'/C4', DMT), 129.04 (CH$_{Ar}$), 130.10 (C2, DMT), 134.93 (C6, Base), 135.16 (C1, DMT), 135.27 (C$_{Ar}$), 144.21 (C1', DMT), 151.34 (C2, Base), 158,79 (C4, DMT), 164.08 (C4, Base), 166.57 (C1), 171.95 (C6), 172.16 (C9).

EXAMPLE 3

Tetrakis-[13-(2'-deoxythymidin-3'-O-yl)-6,9-diaza-2-oxa-5,10,13-trioxotridecyl]-methane (dT$_4$-PE-LPC)

Fractogel® EMD-SO$_3^-$650 (M) (Merck, Darmstadt, Germany) in protonated form (counterion H$^+$) was used for dedimethoxytritylation and solid phase extraction. (DMT-dT)$_4$-PE-LPC (Example 1) (466 mg, 150 µmol) was dissolved in THF/ethanol 95:5 (v/v) and transferred to a column (inner diameter: 20 mm) containing 50 ml ion exchanger, equilibrated with n-hexane/THF 50:50 (v/v). Dimethoxytrityl-compounds were washed of with n-hexane/THF/ethanol 50:50:5 (v/v, 100 ml), THF/ethanol 95:5 (v/v, 100 ml) and THF/Ethanol 50:50 (v/v, 150 ml). dT$_4$-PE-LPC was eluted with pure ethanol, solvent was removed and thoroughly co-evaporation with toluene gave the product as a colorless solid, yield: 93% (263 mg, 139 µmol). $^1$H-NMR (d$_6$-DMSO) δ 1.80 (s, 16 H, CH$_3$—, Base), 2.20 (m, 8 H, H2'), 2.25 (m, 8 H, —CH$_2$CO—), 2.38 (m, 8 H, —COCH$_2$—), 2.52 (m, 8 H, —CH$_2$CO—), 3.08 (m, 16 H, 2×—NHCH$_2$—), 3.21 (s, 8 H, C$_q$CH$_2$O), 3.51 (m, 8 H, —OCH$_2$—), 3.64 (m, 8 H, H5'), 3.98 (m, 4 H, H4'), 5.22 (m, 4 H, H3'), 6.18 (dd, 4 H, H1'), 7.75 (s, 4 H, CH, Base), 7.80/7.85 (dd, 2×4 H, 2×—NH—CH$_2$—). $^{13}$C-NMR (d$_6$-DMSO) δ 12.18 (CH$_3$, Base), 29.02 (C12), 29.94 (C11), 36.06(C4), 36.41 (C2'), 38.35 (C8), 38.84 (C7), 44.70 (C$_q$), 61.27 (C5'), 67.19 (C3), 69.00 (C1), 74.68 (C3'), 83.64/84.50 (C1'/C4'), 109.64 (C5, Base), 135.73 (C6, Base), 150.39 (C2, Base), 163.58 (C4, Base), 170.30 (C5), 170.75 (C10), 171.94 (C13).

EXAMPLE 4

1,3,5-Tris-[9-(2'-deoxythymidin-3'-O-yl)-2,5-diaza-1,6,9-trioxononyl]-benzene (dT$_3$-Aryl-LPC)

Procedure 1

Dedimethoxytritylation and solid phase extraction with Fractogel® EMD-SO$_3^-$650 (M) (counterion H$^+$), additional purification with gel permeation chromatography using Sephadex LH20: (DMT-dT)$_3$-Aryl-LPC (Example 2) (1.1 g, 500 µmol) was dissolved in THF/ethanol 99:1 (v/v) and transferred to a column (inner diameter: 30 mm), containing 150 ml ion exchanger, equilibrated with n-hexane/THF/ethanol 60:35:5 (v/v). Dimethoxytrityl-compounds were washed of with n-hexane/THF/ethanol 60:35:5 (v/v, 200 ml), THF/n-hexane/ethanol 60:35:5 (v/v, 200 ml) and THF/ethanol 95:5 (v/v, 200 ml). dT$_3$-Aryl-LPC was eluted with THF/ethanol 65:35 and THF/ethanol 50:50 (v/v, 300 ml each). The crude product was purified with gel permeation chromatography on Sephadex LH20 (eluent: THF/isopropanol 80:20 v/v), giving a colorless solid after removal of solvents, yield 82% (530 mg, 410 µmol).

Procedure 2

Dedimethoxytritylation with TFA reagent, purification with solid phase extraction using LiChroprep®-DIOL (Merck): (DMT-T)$_3$-Aryl-LPC (Example 2) (580 mg, 260 µmol) was dissolved in (10 ml) 1,2-dichloroethane/nitromethane/methanol 80:19:1 (v/v) and TFA solution in the same solvent system was added (3%, 7.85 mmol TFA, 20 ml). After 3 minutes the reaction mixture was transferred to a column (inner diameter: 25 mm) filled with LiChroprep®-DIOL (90 ml), equilibrated with dichloromethane/ethanol 95:5 (v/v). The same solvent mixture was used for elution of dimethoxytrityl compounds (300 ml). Washing with dichloromethane/pyridine/ethanol 50:40:10 (v/v) gave the product dT$_3$-Aryl-LPC after removal of solvents and co-evaporation with toluene (2×20 ml) as a colorless crystalline solid, yield: 97% (330 mg, 252 µmol).

Procedure 3

Dedimethoxytritylation with TFA reagent, purification by gel permeation chromatography using Sephadex LH20 and additional precipitation in diethyl ether: A TFA solution in 1,2-dichloroethane/nitromethane/methanol 80:19:1 (v/v, 2% TFA, 10 mmol) was dropwise mixed with a solution of (DMT-dT)$_3$-Aryl-LPC (Example 2) (739 mg, 330 µmol) in the same solvent system (5 ml) under stirring at room temperature. After 2 minutes the reaction mixture was cooled in an ice bath and triethylamine (10 mmol in 4 ml of the solvent system) was added. Solvents were removed under reduced pressure and the residue dissolved in N,N-dimethylformamide (5 ml). After chromatography on Sephadex LH20 (eluent: THF/water 70:30, v/v) the most product containing fractions were contaminated with traces of dimethoxytrityl compounds. After removal of the solvents and co-evaporation with dioxane (40 ml), the residue was dissolved in THF/methanol (10 ml) and precipitated into heavily stirred diethyl ether (300 ml). Decantation of the ether layer, filtration of the precipitate under washing with diethyl ether and co-evaporation with pyridine (5 ml) and toluene (2×10 ml) gave dT$_3$-Aryl-LPC as a colorless solid, yield: 88% (380 mg, 290 µmol).

Procedure 4

Dedimethoxytritylation with TFA reagent and neutralization with trioctylamine, purification by chromatography using NUCLEOPREP 300-30 C$_{18}$: (DMT-dT)$_3$-Aryl-LPC (Example 2) (113 mg, 50 µmol) was dissolved in 1,2-dichloroethane/nitro-methane/methanol 80:19:1 (v/v, 4 ml) and a TFA solution in the same solvent system (1.5 mmol TFA in 1 ml) was added dropwise. After 3 minutes the reaction mixture was cooled in an ice bath and neutralized by trioctylamine (1.5 mmol in 1 ml of the solvent system). Solvents were removed under reduced pressure and the residue dissolved in acetonitrile/THF/water 56:14:30 (v/v, 4 ml), also the eluent in the following chromatography using NUCLEOPREP 300-30 C18 (column: 310×20 mm, flow 10 ml/min). Product is present in fractions with a retention time between 7 and 9 minutes and well separated of all other components of the probe. After removal of solvents under reduced pressure and lyophilization with dioxane dT$_3$-Aryl-LPC is obtained as a colorless solid, yield: 98% (64 mg, 49 µmol).

Procedure 5

Dedimethoxytritylation with TFA reagent, purification by combined chromatography using NUCLEOPREP 300-30 C18 and Sephadex LH20: (DMT-dT)$_3$-Aryl-LPC (Example 2) (850 mg, 384 µmol) was dissolved in 1,2-dichloroethane/nitro-methane/methanol 80:19:1 (v/v, 33 ml) and mixed with a TFA solution in the same solvent mixture (11.5 mmol TFA in 10 ml). After 2 minutes a triethylamine solution was added for neutralization under cooling in an ice bath (11.5 mmol, 5 ml in the same solvent system). The reaction mixture was concentrated under reduced pressure and dissolved with the eluent THF/water 60:40 (v/v, 5 ml). Chromatography was performed with a precolumn filled with NUCLEOPREP 300-30 C18 (310×20 mm) and a second column with Sephadex LH20 (460×30 mm, flow: 1 ml/min). Product containing fractions were combined, concentrated and co-evaporated with dioxane (2×40 ml). Final lyophilization with dioxane (10 ml) gave dT$_3$-Aryl-LPC as a colorless solid, yield: 97% (490 mg, 374 µmol). $^1$H-NMR (400 MHz, d$_6$-DMSO) δ 1.78 (s, 9 H, CH$_3$—, Base), 2.25 (m, 6 H, H2'), 2.40 (m, 6 H, —COCH$_2$—), 2.55 (m, 6 H, —CH$_2$CO—), 3.24/3.34 (m, 12 H, 2×—NHCH$_2$—), 3.60 (m, 6 H, H5'), 3.97 (m, 3 H, H4'), 5.20 (m, 3 H, H3'), 6.17 (dd, 3 H, H1'), 7.70 (s, 3 H, CH, Base), 8.00 (dd, 3 H, —NHCH$_2$—), 8.40 (s, 3 H, CH$_{Ar}$), 8.68 (dd, 3 H, —NHCH$_2$). $^{13}$C-NMR (100 MHz, d$_6$-DMSO) δ 12.19 (CH$_3$, Base), 29.02 (C8), 29.76 (C7), 36.38 (C2'), 38.18 (C4), 39.13 (C3), 61.26 (C5'), 74.68 (C3'), 83.60/84.47 (C1'/C4'), 109.64 (C5, Base), 128.48 (CH$_{Ar}$), 134.78 (C$_{Ar}$), 135.74 (C6, Base), 150.39 (C2, Base), 163.57 (C4, Base), 165.51 (C1), 170.79 (C6), 171.95 (C9).

EXAMPLE 5

Tris-{3-aza-4,7-dioxo-7-[5'-O-(4,4'-dimethoxytriph-enylmethyl)-2'-deoxythymidine-3'-O-yl]-heptyl}-amine ((DMT-dT)$_3$-Amine-LPC)

To a solution of 5'-O-dimethoxytrityl-deoxythymidine-3'-p-nitrophenylsuccinate (approx. 9.4 mmol) in dioxane/pyridine a solution of tris-(2-aminoethyl)-amine (292 mg, 2 mmol) in dried acetonitrile (10 ml) was added and stirred for 12 h at room temperature. The reaction mixture was concentrated and the residue dissolved in dichloromethane (containing 0.5% pyridine). Silica gel column chromatography was started with dichloromethane/methanol (0.5% pyridine), increasing the methanol content stepwise up to 15%. Product containing fractions were combined, concentrated and precipitated into n-hexane/diethyl ether 3:1 (v/v). (DMT-dT)$_3$-Amine-LPC was isolated by filtration as a colorless solid, yield: 74% (2.99 g, 1.48 mmol). $^1$H-NMR (CDCl$_3$) δ 1.35 (s, 9 H, CH$_3$—, Base), 2.40/2.50 (m, 6 H, H2'), 2.50/2.52/2.62 (m, 3×6 H, —COCH$_2$—, —CH$_2$N$_{central}$, —CH$_2$CO—), 3.23 (m, 6 H, —CONHCH$_2$—), 3.45 (m, 6 H, H5'), 3.76 (s, 18 H, CH$_3$O—), 4.15 (m, 3 H, H4'), 5.40 (m, 3 H, H3'), 6.38 (dd, 3 H, H1'), 6.8–7.4 (m, 39 H, H$_{Ar}$), 7.58 (CH, Base), 9.55 (NH, Base). $^{13}$C-NMR (CDCl$_3$) δ 11.60 (CH$_3$, Base), 29.77 (C6), 30.46 (C5), 37.75/37.75 (C2'/C2), 54.63 (C1), 55.26 (—OCH$_3$), 63.88 (C5'), 75.89 (C3'), 83.84/84.39 (C1'/C4'), 87.19 (C$_Z$, DMT), 111.89 (C5, Base), 113.35 (C3, DMT), 127.21/128.04/128.23 (C2'/C3'/C4', DMT), 130.08 (C2, DMT), 135.18 (C1, DMT), 135.39 (C6, Base), 144.24 (C1', DMT), 150.91 (C2, Base), 158.78 (C4, DMT), 163.87 (C4, Base), 171.77 (C4), 172.25 (C7).

EXAMPLE 6

Tris-[3-aza-7-(2'-deoxythymidine-3'-O-yl)-4,7-di-oxoheptyl]-amine (dT$_3$-Amine-LPC)

Dedimethoxytritylation of (DMT-dT)$_3$-Amine-LPC (Example 5) (660 mg, 325 µmol) was performed with TFA (2%) in nitromethane/methanol (96:2, v/v, 40 ml). Purification was achieved by solid phase extraction using LiChroprep®-NH$_2$ (Merck, 50 ml, column: 150×20 mm). Dimethoxytrityl compounds were eluted with n-hexane/ethyl acetate 2:1 (v/v, 50 ml), the nucleotidic compounds with ethyl acetate/ethanol 2:1 (v/v, 150 ml). Product containing fractions were concentrated and gel permeation chromatography was used for further purification (Sephadex LH60, eluent: THF/ethanol 90:10, v/v; column: 310×25 mm, flow 1 ml/min). dT$_3$-Amine-LPC was isolated as a colorless solid, yield: 61% (220 mg, 197 µmol). $^1$H-NMR (d$_6$-DMSO) δ 1.77 (s, 9 H, CH$_3$—, Base), 2.25 (m, 6 H, H2'), 2.40 (m, 6 H, —COCH$_2$—), 2.48 (m, 6 H, —CH$_2$N$_{central}$), 2.55 (m, 6 H,—CH$_2$CO), 3.08 (m, 6 H, —CONHCH$_2$—), 3.62 (m, 6 H, H5'), 3.98 (m, 3 H, H4'), 5.18 (m, 3 H, H3'), 6.18 (dd, 3 H, H1'), 7.72 (CH, Base), 7.75 (dd, 3 H,—NHCH$_2$—). $^{13}$C-NMR (d$_6$-DMSO) δ 12.18 (CH$_3$, Base), 29.06 (C6), 29.70 (C5), 36.43 (C2'), 36.98 (C2), 53.35 (C1), 61.27 (C5'), 74.67 (C3'), 83.63/84.51 (C1'/C4'), 109.63 (C5, Base), 135.72 (C6, Base), 150.38 (C2, Base), 163.57 (C4, Base), 170.59 (C4), 171.94 (C7).

EXAMPLE 7

Synthesis of d(5'-O-DMT-G$^{ib}$pA$^{bz}$pC$^{bz}$pG$^{ib}$pG$^{ib}$pC$^{bz}$pC$^{bz}$pA$^{bz}$pG$^{ib}$pT)$_3$-Aryl-LPC The 5'-hydroxyl component dT$_3$-Aryl-LPC (Example 4) (228 mg 166 µmol) was co-evaporated with dried pyridine (3×10 ml) and dissolved in the same solvent (10 ml). (DMT)-dG$^{ib}$-phosphoramidite (1.0 g, 1.2 mmol) was submitted in a 100 ml-two-necked reaction flask under argon atmosphere. The solution of the 5'-hydroxyl component and tetrazole (6 ml, 30.8 mg/ml in acetonitrile, 2.6 mmol) were dropped in 500 μl portions via syringe through septum to phosphoramidite. In case of incomplete reaction phosphoramidite as solid and tetrazole solution were added (controlled by TLC). After complete reaction the mixture was concentrated under reduced pressure and condensation products isolated by GPC using Sephadex LH20 (eluent: THF/methanol 80:20 v/v, column: 530×30 mm, flow: 1 ml/min) without oxidation. Product containing fractions were combined, reduced to a volume of 10 ml and oxidized at 0° C. with t-butylhydroperoxide (80% solution in di-t-butylhydroperoxide, 200 μl, 1.5 mmol) for 5 min. After concentrating and intensive drying in vacuo (5'-O-DMT-G$^{ib}$pT)$_3$-Aryl-LPC was obtained as a colorless solid, yield 87% (520 mg, 144 μmol).

d(G$^{ib}$pT)$_3$-Aryl-LPC was analyzed via MALDI-TOF mass spectrometry (M+H$^+$: theoretical mass 2666.39 Da, found: 2678.3 m/z).

According to the above described cycle, the further elongation steps for the synthesis of d(5'-O-DMT-G$^{ib}$pA$^{bz}$pC$^{bz}$pG$^{ib}$pG$^{ib}$pC$^{bz}$pC$^{bz}$pA$^{bz}$pG$^{ib}$pT)$_3$-Aryl-LPC were performed, using the amounts of reagents listed in Table 2. Data of analysis of the intermediates via MALDI-TOF mass spectrometry are listed in Table 3. Over all nine cycles the crude compound d(5'-O-DMT-G$^{ib}$pA$^{bz}$pC$^{bz}$pG$^{ib}$pG$^{ib}$pC$^{bz}$pC$^{bz}$pA$^{bz}$pG$^{ib}$pT)$_3$-Aryl-LPC was obtained in a yield of 33% (54 μmol, 750 mg).

Table 2

The amounts of reagents used in the different reaction steps and cycles in solution synthesis of d(5'-O-DMT-G$^{ib}$pA$^{bz}$pC$^{bz}$pG$^{ib}$pG$^{ib}$pC$^{bz}$pC$^{bz}$pA$^{bz}$pG$^{ib}$pT)$_3$-Aryl-LPC

TABLE 2

The amounts of reagents used in the different reaction steps and cycles in solution synthesis of d(5'-O-DMT-G$^{ib}$pA$^{bz}$pC$^{bz}$pG$^{ib}$pG$^{ib}$pC$^{bz}$pC$^{bz}$pA$^{bz}$pG$^{ib}$pT)$_3$-Aryl-LPC

| | | 5'-hydroxyl-component: | phosphor-amidite: | tetrazole: | t-BuOOH: | yield: | dedimethoxy-trityl.:TFA/ET$_3$N | yield: |
|---|---|---|---|---|---|---|---|---|
| 1. | cycle 81% | 166 μmol in 10 ml pyridine | 2 g (dG$^{ib}$) 2.4 mmol 5 eq. | 12 ml 5.2 mmol 10 eq. | 200 μl 1.5 mmol 3 eq. | 520 mg 144 μmol 87% | 1.14/2.1 ml 15 mmol 30 eq. | 360 mg 135 μmol 94% |
| 2. | cycle 81% | 135 μmol in 10 ml pyridine | 3 g (dA$^{bz}$) 3.5 mmol 8.75 equiv. | 18 ml 7.8 mmol 19 equiv. | 200 μl 1.5 mmol 3.7 equiv. | 630 mg 126 μmol 93% | 1.14/2.1 ml 15 mmol 30 equiv. | 450 mg 110 μmol 87% |
| 3. | cycle 91% | 110 μmol in 10 ml pyridine | 1.5 g (dC$^{bz}$) 1.8 mmol 5.5 equiv. | 12 ml 5.2 mmol 16 equiv. | 200 μl 1.5 mmol 4.5 equiv. | 630 mg 100 μmol 91% | 0.57/1.1 ml 7.5 mmol 23 equiv. | 580 mg 100 μmol 99% |
| 4. | cycle 84% | 100 μmol in 10 ml pyridine | 2 g (dC$^{bz}$) 2.4 mmol 8 equiv. | 12 ml 5.2 mmol 17 equiv. | 200 μl 1.5 mmol 5 equiv. | 750 mg 98 μmol 98% | 0.57/1.1 ml 7.5 mmol 25 equiv. | 570 mg 84 μmol 86% |
| 5. | cycle 95% | 84 μmol in 10 ml pyridine | 1.5 g (dG$^{ib}$) 1.8 mmol 7 equiv. | 9 ml 3.9 mmol 15 equiv. | 200 μl 1.5 mmol 6 equiv. | 750 mg 83 μmol 99% | 0.57/1.1 ml 7.5 mmol 30 equiv. | 650 mg 80 μmol 96% |
| 6. | cycle 81% | 80 μmol in 10 ml pyridine | 1.5 g (dG$^{ib}$) 1.8 mmol 7.5 equiv. | 9 ml 3.9 mmol 16 equiv. | 200 μl 1.5 mmol 6 equiv. | 850 mg 80 μmol 99% | 0.57/1.1 ml 7.5 mmol 31 equiv. | 620 mg 65 μmol 81% |
| 7. | cycle 83% | 65 μmol in 10 ml pyridine | 2 g (dC$^{bz}$) 2.4 mmol 12 equiv. | 12 ml 5.2 mmol 26 equiv. | 200 μl 1.5 mmol 7 equiv. | 770 mg 65 μmol 99% | 0.57/1.1 ml 7.5 mmol 38 equiv. | 580 mg 54 μmol 83% |
| 8. | cycle 99% | 54 μmol in 10 ml pyridine | 1.4 g (dA$^{bz}$) 1.6 mmol 10 equiv. | 9 ml 3.9 mmol 24 equiv. | 200 μl 1.5 mmol 10 equiv. | 750 mg 54 μmol 99% | 0.57/1.1 ml 7.5 mmol 46 equiv. | 660 mg 54 μmol 99% |
| 9. | cycle | 54 μmol in 10 ml pyridine | 2 g (dG$^{ib}$) 2.4 mmol 15 equiv. | 12 ml 5.2 mmol 30 equiv. | 200 μl 1.5 mmol 10 equiv. | 750 mg 54 μmol 99% | — | — |

The compound was dedimethoxytritylated with TFA reagent, using dichloromethane instead of 1,2-dichloroethane, following the procedure described in Example 4. The amounts of used reagents are given in Table 2, the chromatographic conditions were the same. The intermediate In Table 3 the MALDI-TOF mass spectrometry data, achieved from monitoring the complete synthesis are listed. The dedimethoxytritylated intermediates were dissolved in THF/water 70:30 (v/v) and mixed with matrix solution in the same solvent (3-hydroxypicolinic acid, 0.7 mol/l). The 5'-hydroxyl components could be satisfactory identified up to cycle 6. Deviations from the calculated mass and mass differences are observed at the last three cycles, probably through the increasing occurrence of side products in synthesis and fragmentation during desorption and ionization, leading to signals, which are strongly broadened.

Table 3

Data achieved from 5'-hydroxyl components via MALDI-TOF mass spectrometry.

TABLE 3

Data achieved from 5'-hydroxyl components via MALDI-TOF mass spectrometry.

| intermediates analyzed after dedimethoxytritylation | theoretical mass [Da] | found: M + H⁺ (m/z) | introduced mass difference |
|---|---|---|---|
| 5'-hydroxyl component in 1. cycle: d(T)₃-Aryl-LPC | 1309.26 | 1325.9 | |
| 5'-hydroxyl component in 2. cycle: d(G$^{ib}$$_p$T)₃-Aryl-LPC | 2666.39 | 2678.3 Δm = 1352 | +(3xdG$^{ib}$$_p$) Δm = 1357 |
| 5'-hydroxyl component in 3. cycle: d(A$^{bz}$$_p$G$^{ib}$$_p$T)₃-Aryl-LPC | 4077.49 | 4093.7 Δm = 1415 | +(3xdA$^{bz}$$_p$) Δm = 1411 |
| 5'-hydroxyl component in 4. cycle: d(C$^{bz}$$_p$A$^{bz}$$_p$G$^{ib}$$_p$T)₃-Aryl-LPC | 5416.54 | 5426.1 Δm = 1332 | +(3xdC$^{bz}$$_p$) Δm = 1339 |
| 5'-hydroxyl component in 5. cycle: d(C$^{bz}$$_p$C$^{bz}$$_p$A$^{bz}$$_p$G$^{ib}$$_p$T)₃-Aryl-LPC | 6755.59 | 6764.6 Δm = 1338 | +(3xdC$^{bz}$$_p$) Δm = 1339 |
| 5'-hydroxyl component in 6. cycle: d(G$^{ib}$$_p$C$^{bz}$$_p$C$^{bz}$$_p$A$^{bz}$$_p$G$^{ib}$$_p$T)₃-Aryl-LPC | 8112.83 | 8112.8 Δm = 1366 | +(3xdG$^{ib}$$_p$) Δm = 1357 |
| 5'-hydroxyl component in 7. cycle: d(G$^{ib}$$_p$G$^{ib}$$_p$C$^{bz}$$_p$C$^{bz}$$_p$A$^{bz}$$_p$G$^{ib}$$_p$T)₃-Aryl-LPC | 9469.11 | 9346.8 Δm = 1234 | +(3xdG$^{ib}$$_p$) Δm = 1357 |
| 5'-hydroxyl component in 8. cycle: dC$^{bz}$$_p$G$^{ib}$$_p$G$^{ib}$$_p$G$^{ib}$$_p$C$^{bz}$$_p$C$^{bz}$$_p$A$^{bz}$$_p$G$^{ib}$$_p$T)₃-Aryl-LPC | 10808.96 | 10774.8 Δm = 1428 | +(3xdC$^{bz}$$_p$) Δm = 1339 |
| 5'-hydroxyl component in 9. cycle: d(A$^{bz}$$_p$C$^{bz}$$_p$G$^{ib}$$_p$G$^{ib}$$_p$G$^{ib}$$_p$C$^{bz}$$_p$C$^{bz}$$_p$A$^{bz}$$_p$G$^{ib}$$_p$T)₃-Aryl-LPC | 12219.97 | 12143.2 Δm = 1368 | +(3xdA$^{bz}$$_p$) Δm = 1411 |

For cleavage of decamer d(GACCGGCAGT) from the liquid phase carrier and for base and phosphate deprotection, the compound d(5'-O-DMT-G$^{ib}$pA$^{bz}$pC$^{bz}$pG$^{ib}$pG$^{ib}$pC$^{bz}$pC$^{bz}$pA$^{bz}$pG$^{ib}$pT)₃-Aryl-LPC (13 mg, 1 µmol) was treated with ammonium hydroxide (32%, 3 ml) for 20 h at 55° C. The characterization of main and side products starts with reversed phase HPLC using the DMT group for separation. 200 µmol were purified using a Waters chromatography system Delta Prep 4000 (column: Whatman, Partisil 10 ODS M9, 500×9.4 mm, 10 µm particles, eluents were: 0.1 M tri-ethylammonium acetate at pH 7.0 (A) and acetonitrile (B), flow: 4 ml/min, 5 to 40% B in 40 min, monitored at 260 nm). Fractions were collected around the peak maximum at 32 min, followed by dedimethoxytritylation with acetic acid (80%, 500 µl). The product was analyzed by ion exchange HPLC using the Pharmacia SMART system (column: Mono Q 1.6/5, eluents were 25 mM tris-HCl, 1 mM EDTA, pH 8.0 (A) and: 25 mM Tris-HCl, 1 mM EDTA, 1 M NaCl, pH 8.0 (B), flow: 100 µl/min: start: 20% B, 4 min isocratic, 20 to 60% B in 26 min) and compared to d(GACCGGCAGT), achieved from solid phase synthesis on CPG with included capping step.

EXAMPLE 8

Synthesis with Dimer Phosphoramidites

The 5'-hydroxyl component dT₃-Aryl-LPC (Example 4) (131 mg, 100 µmol, in 5 ml pyridine) was treated with d(5'-O-DMT-C$^{tl}$pC$^{tl}$) phosphoramidite (total: 1.79 g, 1.36 mmol, 4.5 equivalents) in the above described procedures. Instead of 1H-tetrazole, 5-(4-nitrophenyl)-tetrazole was used (1.4 mmol, as suspension in acetonitrile). Oxidation with t-butylhydroperoxide (80% in di-t-butylperoxide, 3.75 mmol, 500 µl, at 0° C.) was performed before GPC with Sephadex LH20 (Eluent: THF/methanol 80:20, same conditions as described above). Yield: 99% crude (5'-O-DMT-C$^{tl}$pC$^{tl}$pT)₃-Aryl-LPC (516 mg, 99 µmol). In the dedimethoxytritylation step, TFA (760 µl) in dichloromethane/nitromethane/methanol 80:19:1 (32 ml, v/v). and triethylamine (1.4 ml at 0° C.) was used. Purification was obtained by the described chromatography using the eluent THF/water 60:40 (v/v) and the precolumn filled with NUCLEOPREP 300-30 C18 (310×20 mm) combined with the second column with Sephadex LH20 (460×30 mm, flow: 1 ml/min). Yield per cycle: 83% (340 mg, 83 µmol d(C$^{tl}$pC$^{tl}$pT)₃-Aryl-LPC). MALDI-TOF-MS: (MH⁺=4108.1 m/z, M$_{calc.}$=4077.56). In the second condensation 4.4 equivalents of d(5'-O-DMT-G$^{DPC/ib}$pC$^{tl}$-phosphoramidite (1.1 mmol, 1.65 g) and 5-(4-nitrophenyl)-tetrazole (1.2 mmol) were used leading to compound d(5'-O-DMT-G$^{DPC/ib}$pC$^{tl}$pC$^{tl}$pC$^{tl}$pT)₃-Aryl-LPC (570 mg, 69 µmol, 83%). Analysis was performed as described above, but varying the eluent conditions in SMART-HPLC (Start: 0% B, 4 min isocratic, 0 to 60% B in 26 min). MALDI-TOF-MS for d(GpCpCpCpT): M+H⁺: 1440.5 m/z (M$_{calc.}$=1435.0 Da), d(GpCpCpCp): M+H⁺: 1194.8 m/z (M$_{calc.}$=1192.8 Da).

Since modifications will be apparent to those of skill in this art, it is intended that this invention be limited only by the scope of the appended claims.

What is claimed is:

1. A liquid phase carrier (LPC) that has formula (Id):

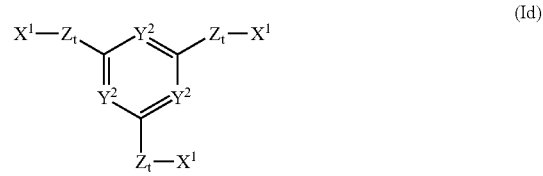

(Id)

wherein: Z is any combination of 1–12 units selected from 1,4-phenylene and methylene units, which units may be combined in any order; t is 1; $X^1$ is OH, SH, NH₂, COR⁵ or COOR⁴ where R⁴ is selected from hydrogen, alkyl, aryl, aralkyl, heteroaryl, heteroaralkyl, heterocyclyl and heterocyclylalkyl, and R⁵ is halide, heteroaryl or pseudohalide; n is 3 or 4; with the proviso that if Z is methylene, then Z contains more than three methylene units; $Y^2$ is CH; $X^1$, $Y^2$ and Z are unsubstituted or substituted with one or more substituents each independently selected from Q; and Q is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl.

2. The LPC of claim 1, wherein Z is a group with three or more points of attachment: one to the cyclic nucleus, and the others to two or more $X^1$ groups.

3. The LPC of claim 1, wherein the LPC has formula (IId):

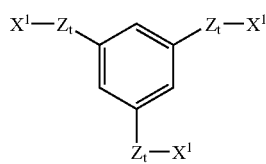

(IId)

4. The LPC of claim 3, wherein $X^1$ is $COR^5$ or $COOR^4$.

5. The LPC of claim 3, wherein $X^1$ is $COOR^4$.

6. The LPC of claim 1 that is coupled to a photocleavable linker.

7. A liquid phase carrier (LPC), selected from the group consisting of 1,3,5-tris{2,5-diaza-9-(5'-O-(4,4'-dimethoxytriphenyl-methyl)-2'-deoxythymidine-3'-O-yl)-1,6,9-trioxononyl}-benzene ((DMT-dT)$_3$-Aryl-LPC), and 1,3,5-tris(9-(2'-deoxythymidin-3'-O-yl)-2,5-diaza-1,6,9-trioxononyl)-benzene (dT$_3$-Aryl-LPC).

8. A method of solution phase biopolymer synthesis, comprising the steps of:
(a) reacting an LPC with a first monomer $N^1$; wherein the LPC has formula (Id):

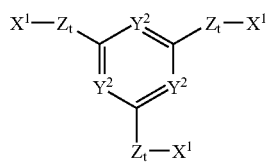

(Id)

wherein: Z is any combination of 0–12 units selected from 1,4-phenylene and methylene, which units may be combined in any order; t is 0 or 1; $X^1$ is OH, SH, NH$_2$, COR$^5$ or COOR$^4$, where R$^4$ is selected from hydrogen, alkyl, aryl, aralkyl, heteroaryl, heteroaralkyl, heterocyclyl and heterocyclylalkyl; and R$^5$ is halide, heteroaryl or pseudohalide; n is 3 or 4; $Y^2$ is CH; $X^1$, $Y^2$ and Z are unsubstituted or substituted with one or more substituents each independently selected from Q; and Q is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl;

(b) separating and purifying the product of step (a);
(c) reacting the product of step (b) with a second monomer N$^2$, a dimer N$^2$–N$^3$ or a trimer N$^2$–N$^3$–N$^4$; and
(d) repeating steps (b) and (c) to produce an LPC-bound biopolymer having m monomers, where m is 3 to 100, wherein:
N$^1$, N$^2$, N$^3$ ... N$^m$ are biopolymer monomers; and
the dimers and trimers comprise the monomers.

9. The method of claim 8, wherein the LPC is selected from the group consisting of 1,3,5-tris{2,5-diaza-9-(5'-O-(4,4'-dimethoxytriphenyl-methyl)-2'-deoxythymidine-3'-O-yl)-1,6,9-trioxononyl}-benzene ((DMT-dT)$_3$-Aryl-LPC), and 1,3,5-tris(9-(2'-deoxythymidin-3'-O-yl)-2,5-diaza-1,6,9-trioxononyl)-benzene (dT$_3$-Aryl-LPC).

10. The method of claim 8, wherein the monomers are nucleotides, nucleosides, natural or unnatural amino acids, protein nucleic acid (PNA) monomers or monosaccharides.

11. A method of solution phase biopolymer synthesis, comprising the steps of:
(a) reacting an LPC with a first monomer N$^1$; wherein the LPC has formula (Id):

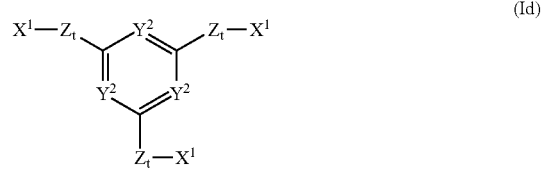

(Id)

wherein: Z is any combination of 0–12 units selected from 1,2-, 1,3- or 1,4-phenylene and methylene, which units may be combined in any order; t is 0 or 1; $X^1$ is OH, SH, NH$_2$, COR$^5$ or COOR$^4$, where R$^4$ is selected from hydrogen, alkyl, aryl, aralkyl, heteroaryl, heteroaralkyl, heterocyclyl and heterocyclylalkyl; and R$^5$ is halide, heteroaryl or pseudohalide; n is 3 or 4; $Y^2$ is CH; $X^1$, $Y^2$ and Z are unsubstituted or substituted with one or more substituents each independently selected from Q; and Q is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl;

(b) separating and purifying the product of step (a);

(c) reacting the product of step (b) with a second monomer $N^2$, a dimer $N^2$–$N^3$ or a trimer $N^2$–$N^3$–$N^4$; and (d) repeating steps (b) and (c) to produce an LPC-bound biopolymer having m monomers, where m is 3 to 100, wherein:

$N^1$, $N^2$, $N^3$ . . . $N^m$ are biopolymer monomers;

the dimers and trimers comprise the monomers; and the protocol used in steps (c) and (d) to synthesize the biopolymer is the phosphoramidite protocol.

12. The LPC of claim 1 coupled to a biopolymer.

* * * * *

UNITED STATES PATENT AND TRADEMARK OFFICE
CERTIFICATE OF CORRECTION

PATENT NO. : 7,038,103 B2
APPLICATION NO. : 09/484484
DATED : May 2, 2006
INVENTOR(S) : Hubert Koster et al.

It is certified that error appears in the above-identified patent and that said Letters Patent is hereby corrected as shown below:

IN THE REFERENCES CITED [56]:
In OTHER PUBLICATIONS:
in Kaldor, S.W. et al., please insert --the-- between "for" and "Purification"
in Khorana, H.G., please insert --a-- between "of" and "Gene"
in Konig, B. et al., please replace "Azamacrocyles:" with --Azamacrocycles:--
in the fourth Köster, H. et al., please replace "Objectives" with --Objective--
in Pon, R.T., please replace "Nitrophonyl" with --Nitrophenyl--
in Schmidt, J.G. et al, please replace "Inforation" with --Information--
in Virnekas, B. et al., please replace "Phosphoramidities:" with --Phosphoramidites:--
in Bradshaw J. and Krakowiak, K., please replace "Azaoxemecrobicyclic" with --Azaoxamacrobicyclic--; and please replace "35:519" with --J. Heterocycl. Chem. 35:519-524--
in Cochrane et al., please replace "1968" with --630-632 (1968):--

UNITED STATES PATENT AND TRADEMARK OFFICE
CERTIFICATE OF CORRECTION

PATENT NO. : 7,038,103 B2
APPLICATION NO. : 09/484484
DATED : May 2, 2006
INVENTOR(S) : Hubert Koster et al.

It is certified that error appears in the above-identified patent and that said Letters Patent is hereby corrected as shown below:

at column 26, line 1-20, the structure should be presented as follows:

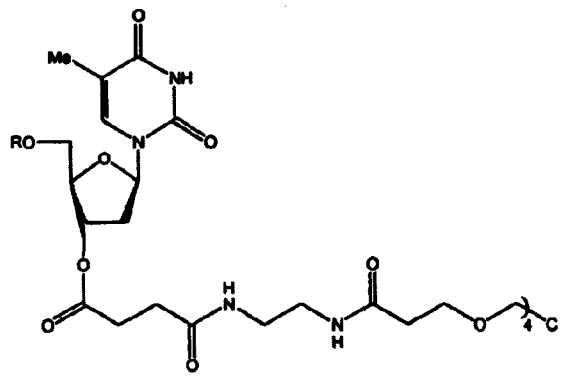

Signed and Sealed this

Twenty-first Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,038,103 B2  Page 1 of 1
APPLICATION NO. : 09/484484
DATED : May 2, 2006
INVENTOR(S) : Hubert Koster et al.

It is certified that error appears in the above-identified patent and that said Letters Patent is hereby corrected as shown below:

IN THE REFERENCES CITED ITEM [56]:
In OTHER PUBLICATIONS:
in Kaldor, S.W. et al., please insert --the-- between "for" and "Purification"
in Khorana, H.G., please insert --a-- between "of" and "Gene"
in Konig, B. et al., please replace "Azamacrocyles:" with --Azamacrocycles:--
in the fourth Köster, H. et al., please replace "Objectives" with --Objective--
in Pon, R.T., please replace "Nitrophonyl" with --Nitrophenyl--
in Schmidt, J.G. et al., please replace "Inforation" with --Information--
in Virnekas, B. et al., please replace "Phosphoramidities:" with --Phosphoramidites:--
in Bradshaw J. and Krakowiak, K., please replace "Azaoxemecrobicyclic" with
  --Azaoxamacrobicyclic--; and please replace "35:519" with
  --J. Heterocycl. Chem. 35:519-524--
in Cochrane et at., please replace "1968" with --630-632 (1968)--

IN THE SPECIFICATION:
at column 11, line 50, please replace
  "-Sp-O–$C_6H_4(C_6H_5)_2$C–OH (-->-Sp-O–$C_6H_4(C_6H_5)_2$C–Cl" with
  -- -Sp-O–$C_6H_4(C_6H_5)_2$C–OH-->-Sp-O–$C_6H_4(C_6H_5)_2$C–Cl --

Signed and Sealed this

Ninth Day of January, 2007

JON W. DUDAS
*Director of the United States Patent and Trademark Office*